US008158152B2

(12) United States Patent
Palepu

(10) Patent No.: US 8,158,152 B2
(45) Date of Patent: Apr. 17, 2012

(54) LYOPHILIZATION PROCESS AND PRODUCTS OBTAINED THEREBY

(75) Inventor: Nageswara R. Palepu, Mill Creek, WA (US)

(73) Assignee: SciDose LLC, Amherst, MA (US)

( * ) Notice: Subject to any disclaimer, the term of this patent is extended or adjusted under 35 U.S.C. 154(b) by 1560 days.

(21) Appl. No.: 11/282,507

(22) Filed: Nov. 18, 2005

(65) Prior Publication Data

US 2007/0116729 A1    May 24, 2007

(51) Int. Cl.
*A61K 9/14* (2006.01)
(52) U.S. Cl. .......... 424/489; 514/35; 514/291; 514/192; 514/200; 514/282
(58) Field of Classification Search .................. None
See application file for complete search history.

(56) References Cited

U.S. PATENT DOCUMENTS

| | | | |
|---|---|---|---|
| 4,959,215 A | 9/1990 | Sauerbier et al. |
| 5,206,025 A | 4/1993 | Courteille et al. |
| 5,336,669 A | 8/1994 | Palepu et al. |
| 5,418,223 A | 5/1995 | Palepu et al. |
| 5,424,471 A | 6/1995 | Kennedy et al. |
| 5,561,121 A | 10/1996 | Ku et al. |
| 5,591,731 A | 1/1997 | Kennedy et al. |
| 5,612,058 A | 3/1997 | Schutz et al. |
| 5,631,023 A | 5/1997 | Kearney et al. |
| 5,731,291 A | 3/1998 | Sullivan et al. |
| 5,882,684 A | 3/1999 | Schutz et al. |
| 5,955,488 A | 9/1999 | Winterborn |
| 6,010,719 A | 1/2000 | Remon et al. |
| 6,063,802 A | 5/2000 | Winterborn |
| 6,133,440 A | 10/2000 | Qiu et al. |
| 6,207,456 B1 | 3/2001 | Baru et al. |
| 6,271,214 B1 | 8/2001 | Qiu et al. |
| 6,384,259 B1 | 5/2002 | Stogniew et al. |
| 6,407,278 B2 | 6/2002 | Stogniew et al. |
| 6,436,679 B1 | 8/2002 | Qiu et al. |
| 6,440,414 B1 | 8/2002 | Kendrick et al. |
| 6,489,312 B1 | 12/2002 | Stogniew et al. |
| 6,566,329 B1 | 5/2003 | Meyn et al. |
| 6,576,651 B2 | 6/2003 | Bandyopadhyay et al. |
| 6,586,574 B1 | 7/2003 | Hansen |
| 6,589,554 B1 | 7/2003 | Mizumoto et al. |
| 6,641,526 B1 | 11/2003 | Wakayama |
| 6,670,384 B2 | 12/2003 | Bandyopadhyay et al. |
| 6,746,694 B1 | 6/2004 | Bhadra et al. |
| 6,770,678 B1 | 8/2004 | Kurz |
| 6,803,054 B2 | 10/2004 | Mizumoto et al. |
| 6,841,545 B2 | 1/2005 | Stogniew et al. |
| 6,869,618 B2 | 3/2005 | Kiel et al. |
| 6,884,422 B1 | 4/2005 | Liu et al. |
| 6,900,184 B2 | 5/2005 | Cohen et al. |
| 2002/0010357 A1 | 1/2002 | Stogniew et al. |
| 2002/0091270 A1 | 7/2002 | Wu et al. |
| 2002/0143038 A1 | 10/2002 | Bandyopadhyay et al. |
| 2002/0155097 A1 | 10/2002 | Tei |
| 2003/0068416 A1 | 4/2003 | Burgess et al. |
| 2003/0077321 A1 | 4/2003 | Kiel et al. |
| 2003/0082236 A1 | 5/2003 | Mathiowitz et al. |
| 2003/0096378 A1 | 5/2003 | Qiu et al. |
| 2003/0096797 A1 | 5/2003 | Stogniew et al. |
| 2003/0113316 A1 | 6/2003 | Kaisheva et al. |
| 2003/0191157 A1 | 10/2003 | Doen |
| 2003/0202978 A1 | 10/2003 | Maa et al. |
| 2003/0211042 A1 | 11/2003 | Evans |
| 2003/0229027 A1 | 12/2003 | Eissens et al. |
| 2004/0005351 A1 | 1/2004 | Kwon |
| 2004/0042971 A1 | 3/2004 | Truong-Le et al. |
| 2004/0042972 A1 | 3/2004 | Truong-Le et al. |
| 2004/0043042 A1 | 3/2004 | Johnson et al. |
| 2004/0057927 A1 | 3/2004 | Warne et al. |
| 2004/0063792 A1 | 4/2004 | Khera et al. |
| 2004/0092587 A1 | 5/2004 | Takada et al. |
| 2004/0157789 A1 | 8/2004 | Geall et al. |
| 2004/0167173 A1 | 8/2004 | Reddy et al. |
| 2004/0176357 A1 | 9/2004 | Dekemper |

(Continued)

FOREIGN PATENT DOCUMENTS

WO    WO99-30688    6/1999

(Continued)

OTHER PUBLICATIONS

Jiang Guokun et al, Preparation of crystalline acyclovir sodium for injection, *Chinese Journal of Pharmaceuticals*, 2002, 33(2): 79-80).

*Primary Examiner* — Robert A Wax
*Assistant Examiner* — Hasan Ahmed
(74) *Attorney, Agent, or Firm* — Frommer Lawerence & Haug LLP; Sandra Kuzrnich, Esq.; Russell A. Garman

(57) ABSTRACT

A lyophilization process which comprises dissolving a material in one or more solvents for said material to form a solution; forcing said material at least partially out of solution by combining the solution and a non-solvent for the material, which non-solvent is miscible with the solvent or solvents used and wherein said non-solvent is volatilizable under freeze-drying conditions. In addition, for hydrophobic and/or lipophilic materials, the anti-solvent can be omitted, and the solution of the material in the solvent can be subjected directly to freeze drying. The lyophilizates can then be reconstituted with typical aqueous diluent in the case of hydrophilic materials. Hydrophobic and or lipophilic materials can be initially reconstituted with propylene glycol and/or polyethyleneglycol to form a high concentration solution therein and this is further diluted for use with a diluent of Intralipid, plasma, serum, or even whole blood.

46 Claims, No Drawings

U.S. PATENT DOCUMENTS

| | | |
|---|---|---|
| 2004/0197885 A1 | 10/2004 | Ueda |
| 2004/0234593 A1 | 11/2004 | Kierl et al. |
| 2004/0235903 A1 | 11/2004 | Khanna |
| 2005/0020509 A1 | 1/2005 | Kiel et al. |
| 2005/0020610 A1 | 1/2005 | Zhang et al. |
| 2005/0020615 A1 | 1/2005 | Rubino |
| 2005/0032775 A1 | 2/2005 | Gyollai et al. |
| 2005/0037067 A1 | 2/2005 | Hovdal et al. |
| 2005/0049209 A1 | 3/2005 | Chen |
| 2005/0063912 A1 | 3/2005 | Montgomery et al. |
| 2005/0069578 A1 | 3/2005 | Balasubramanian et al. |
| 2005/0069584 A1 | 3/2005 | Kiel et al. |
| 2005/0084530 A1 | 4/2005 | Rao |
| 2005/0100598 A1 | 5/2005 | Mizumoto et al. |
| 2005/0137265 A1 | 6/2005 | Haley |
| 2005/0142190 A1 | 6/2005 | Adin et al. |
| 2005/0148597 A1 | 7/2005 | Kostanski et al. |
| 2005/0152962 A1 | 7/2005 | Metselaar |
| 2005/0152980 A1 | 7/2005 | Ausborn et al. |
| 2005/0152981 A1 | 7/2005 | Gleeson et al. |

FOREIGN PATENT DOCUMENTS

| | | |
|---|---|---|
| WO | WO2004-039804 | 5/2004 |

LYOPHILIZATION PROCESS AND PRODUCTS OBTAINED THEREBY

CROSS-REFERENCE TO RELATED APPLICATIONS

Not applicable.

STATEMENT REGARDING FEDERALLY SPONSORED RESEARCH OR DEVELOPMENT

Not Applicable

FIELD OF THE INVENTION

The present invention relates to methods of preparing lyophilizates, especially those free of undesired extra components. The invention further relates to obtaining lyophilizates of amorphous/crystalline solids that are rapidly reconstitutable. The invention further relates to the materials resulting from the novel lyophilization techniques presented herein.

BACKGROUND OF THE INVENTION

Freeze-drying or lyophilization has been widely used for a number of decades in pharmaceutical, food, and chemical industries. Freeze-drying is particularly desirable in situations where a pharmaceutical or other material is required to be dried or dehydrated or desolvated, but is sensitive to the application of heat for the purpose of drying. Many compounds, when exposed to the typically employed drying temperatures of non-freeze drying techniques, decompose, degrade, or volatilize away, resulting in an undesirable product. To recognize the large number of applications to which freeze-drying has been adapted, one need only run a simple search of the US Patent and Trademark Office patent databases for the term "freeze drying" and/or "lyophilization", which as of October 2005, returns over 3000 hits and covers a wide range of active agents and other materials.

In general, the freeze-drying or lyophilization technique is to dissolve, suspend, or emulsify a compound or formulation; freeze the resultant solution, suspension, or emulsion; and then to apply a vacuum thereto to sublimate/evaporate the solvents and other liquids in the frozen mass used to dissolve, suspend or emulsify the material. In many applications, the use of auxiliary agents to create suitable solutions, suspensions, and emulsions is not of significant concern. This is especially so where the auxiliary agent is acceptable to be present in the end product, as in the use of auxiliary food ingredients in freeze dried foods. Similarly, where pharmaceuticals are intended for oral ingestion, a wide range of auxiliary pharmaceutically acceptable agents may be used to aid in the preparation of lyophilized active compounds or formulations containing such active compounds. In most freeze-drying processes, a clear solution of the material to be freeze dried is obtained, if possible. This is then usually filtered aseptically to remove any extraneous solids and microorganism, and the filtered solution is filled into glass vials and cooled in a lyophilization chamber whereby the dissolved solids generally freeze together with the freezable liquid components, but may, depending upon concentration and the rate of the freezing process, begin to come out of solution during the process of cooling or freezing. For example, if one were to prepare a solution at its saturation concentration, the dissolved solid could precipitate during the freezing process. Depending upon the solvent or solvent combination used, there may be some liquid portion that does not freeze, but remains liquid and is distributed within the otherwise frozen mass. The application of vacuum pressures then permits the removal of unfrozen liquids first, followed by the sublimation of frozen liquid components, leaving behind a purer, dried product. In some techniques, the freezing process is done slowly so that crystallization takes place substantially before the solvent is frozen. In other techniques, the freezing step is performed rapidly to freeze the solvent before appreciable crystallization has occurred. In still other techniques, after freezing has taken place, addition of a small degree of heat to warm the frozen mass slightly permits the frozen liquid components to sublimate more readily. These same techniques may be applicable to situations when suspensions, emulsions, and complex formulations are involved, except that the filtering step may not be suitable because it may remove active or other auxiliary components which are intended to be present.

Unfortunately, the range of acceptable materials for use in pharmaceuticals that are intended for parenteral administration, is not as large and not so accommodating. For example, emulsions where the freeze-drying process leaves the emulsifier and/or the oil phase present in the lyophilizate would generally not be acceptable from an intravenous injection point of view. Similarly, suspending agents would also not be desirable. Thus, it is clear that an alternate lyophilization procedure that could eliminate the use of undesirable auxiliary agents to a larger degree than is presently available is desirable and sought after.

Although the prior art is replete with references to freeze-drying and lyophilization, most literature refers to the technique in a general manner such as "the material is freeze-dried as commonly practiced in the art" and other general statements of similar description. Virtually all of the references that do describe the details of the lyophilization process make no mention of, nor suggestion of, the use of an anti-solvent or non-solvent. Most references refer to clear solutions, solvents and co-solvents being used to obtain clarity or near clarity, with the solution then being filtered. Most references involving lyophilization, when discussing solvents, refer to aqueous materials.

Representative (non-exhaustive) patents and applications which are of note include the following, all of which are incorporated herein in their entirety. U.S. 2005/0049209 discusses freeze-drying of emulsions. U.S. Pat. No. 6,770,678 discusses that for freeze drying purposes it is desirable to have the solution concentration as high as possible, but often the high concentration leads to crystals forming during the cooling step, which the reference states is undesirable. U.S. 2004/0063792 mentions freeze-drying sertraline from a number of solvent/co-solvent combinations. U.S. 2004/0043042 discusses micro-lyophilization. U.S. 2003/0229027 mentions freeze-drying canabinoids from solvent mixtures in the presence of certain sugars. U.S. 2003/0202978 discusses spray freeze-drying. U.S. 2002/0010357; U.S. Pat. Nos. 6,384,259; 6,407,278; 6,841,545; and 6,489,312 all relate to amifostine lyophilizates. U.S. Pat. No. 6,566,329 discusses precipitating human growth hormone out of solution by adjusting the pH to the isoelectric point and then freeze-drying the result. U.S. Pat. No. 5,731,291 discusses using a solvent (water) and a second agent that sublimates at −40° C. in a lyophilization process. WO99/30688 discusses using an accelerant excipient to enhance the rate of solvent sublimation. WO2004/039804 discusses freeze-drying moxifloxacin from water. The specification mentions that it can also be obtained by use of an anti-solvent followed by filtration, decantation, or centrifugation. There is no suggestion that the moxifloxacin obtained from the solution by use of an anti-solvent then be subjected to freeze drying. U.S. 2003/082236 discusses use of a supercritical anti-solvent.

OBJECTS OF THE INVENTION

It is therefore an object of the invention whereby a hydrophilic or a hydrophobic material may be lyophilized using a minimum number of auxiliary materials.

It is another object of the invention to prepare lyophilizates of water sensitive materials.

It is still another object of the invention whereby an amorphous material may be recovered via lyophilization with or without the use of auxiliary agents.

Still another object of the invention is to provide a non-aqueous lyophilization technique which includes several organic solvents which have not been previously known for use in the lyophilization process art.

It is still another object of the invention whereby a crystalline hydrate and/or amorphous material may be recovered via lyophilization without the use of auxiliary agents while simultaneously avoiding the use of ethanol.

An even further object of the invention is to provide a method of obtaining a substantially pure, readily reconstitutable hydrophilic or hydrophobic or lipophilic material substantially free of auxiliary materials.

An even further object of the invention is to provide a method of obtaining a substantially pure, readily reconstitutable hydrophilic or hydrophobic or lipophilic material substantially free of auxiliary materials which when reconstitutes with pharmaceutically acceptable diluent will result in either a clear solution or a micellar solution or an emulsion or a sub-micron suspension.

An even further object of the invention is to provide a method of obtaining a substantially pure, readily reconstitutable material containing a hydrophobic or lipophilic substance that further contains at least one of a solubilizer or a surfactant or combinations thereof which material, upon reconstitution with pharmaceutically acceptable diluent will result in either a clear solution or a micellar solution or an emulsion or a sub-micron suspension.

Yet another object of the invention is to provide a method for obtaining an amorphous lyophilizate which is stable in the presence of moisture.

An even further object of the invention is to provide a method of obtaining crystalline hydrate lyophilizates that are stable in the presence of moisture.

Yet another object of the invention is to prepare stable lyophilizates of water sensitive materials from a lyophilization process that includes water.

A further object of the invention is provide new, simplified lyophilization procedures for lipophilic and/or hydrophobic materials, with or without the use of anti-solvents.

An even further object of the invention is to provide novel lyophilizates of lipophilic and/or hydrophobic materials.

Still a further object of the invention is to provide novel reconstitution methods for lyophilizates of lipophilic and/or hydrophobic materials.

An even further object is to provide a rapidly dissolving end-used product that is suitable for use in delivering single unit dosages of in excess of hundreds of milligrams.

Still other objects of the invention will be apparent to those of ordinary skill in the art.

BRIEF SUMMARY OF THE INVENTION

These and other objects of the invention are surprisingly achieved by a process which comprises dissolving the material in one or more solvents for said material to form a solution; forcing said material at least partially out of solution by combining the solution and a non-solvent for the material, which non-solvent is miscible with the solvent or solvents used and wherein said non-solvent is volatilizable under freeze-drying conditions or optionally seeding the solution before or during the step of forcing it out of solution; freezing the result thus far; and applying a vacuum to dry the frozen result. For hydrophilic substances water is frequently the primary solvent and forms the frozen mass while any co-solvent and the anti-solvent may or may not freeze during the freezing step. For lipophilic or hydrophobic materials, water is frequently the anti-solvent and it is the solvent and potential co-solvent which may or may not freeze during the freezing step. Either way, the dissolved material is forced out of solution by the anti-solvent, the result subjected to freezing temperatures to form a frozen mass, and the frozen mass subjected to vacuum pressures to result in a lyophilizate. In addition, for hydrophobic and/or lipophilic materials, the anti-solvent can be omitted, and the solution of the material in the solvent can be subjected directly to freeze drying. The lyophilizates can then be reconstituted with typical aqueous diluent in the case of hydrophilic materials. Hydrophobic and or lipophilic materials can be initially reconstituted with propylene glycol and/or polyethyleneglycol to form a high concentration solution therein and this is further diluted for use with a diluent of Intralipid, plasma, serum, or even whole blood.

DETAILED DESCRIPTION OF THE INVENTION

The present invention is directed to a method for freeze-drying or lyophilizing a material which may be (i) hydrophilic or (ii) hydrophobic and/or lipophilic. Generally when the material is hydrophilic, the material is also sensitive to the presence of moisture. The material is usually a substantially pure compound, preferably a pure compound, but may also be a simple or complex mixture. The material is dissolved in a solvent therefor, preferably without, but potentially with, one or more co-solvents so as to obtain a substantially clear, preferably clear, solution of said material therein. Solvent for the material is one which can be removed in a freeze-drying process, i.e., one that is volatile or sublimates at the temperature and pressure used in the primary drying step with any residual amount being removable during a secondary drying step. If desired, the solution may be filtered aseptically before combining it with the anti-solvent which is also filtered aseptically, to remove any undesired (or undissolved) materials as well as microorganisms from the material containing solution and anti-solvent. Alternatively, a pH adjustment can be effected prior to the optional filtration in order to aid stability and/or solubility, and/or post filtration to aid stability. Preferably, a pH adjustment for stability purposes, when used, is conducted before the optional filtration step. The pH adjustment can be accomplished by the addition of an acid or a base or a buffer. Once the material to be lyophilized is in solution, the solution is subjected to an anti-solvent for the material (or a mixture of anti-solvents for the material). The anti-solvent for the material is volatile or sublimates under lyophilization conditions (i.e., at the pressure and temperature used in the primary drying step). If the anti-solvent doesn't freeze under lyophilization conditions, special lyophilization techniques are adopted (such as the inclusion of a liquid nitrogen trap between the condenser and vacuum pump, and the like) to remove the anti-solvent. The anti-solvent is not a solvent for the material and the material is essentially insoluble in the anti-solvent but is miscible with the solvent used to dissolve (and any co-solvent that is present to dissolve) the material so that upon its addition, a substantial portion preferably substantially all, most preferably all, of the material is forced out of solution and forms a suspension or slurry of solid particulates in the complex solvent/optional co-solvent/anti-solvent mixture. Optionally before or during, preferably before or at the beginning of, the step when the material is forced out of solution, the solution may be seeded with a portion of the material that is in the desired solid form to enhance formation of the appropriate form of the material. Optionally, if desired, the result can then be filtered, decanted, etc. to separate a portion of the solvent/optional co-solvent/anti-solvent mixture from the precipitated solids. When such a separation technique is used, the separated solids are still wet with the solvent/optional co-solvent/anti-solvent mixture. Whether or not the post precipitation separation technique is used, the resulting wet solids (suspension, slurry, etc.) are then frozen and the frozen solid is dried by the application of vacuum to remove the solvent, the co-solvent, and the anti-solvent. In some embodiments, one or more (but not all) of the solvent/optional co-solvent/anti-solvent of choice does not freeze at the freezing step temperature allowed by the lyophilizer. When this is the case, special anti-solvent removal conditions need to be used. These special removal conditions include the use of a liquid nitrogen trap and other similar techniques known in the art.

The material may be selected from a wide range of compounds and compositions, but is preferably a substantially pure compound, most preferably a pure compound, where "pure" indicates as reasonably pure as can be obtained using at least commercially reasonable standards and tolerances. Thus, a product is "pure" for purposes of this invention if (in the context of pharmaceutical materials) it is sufficiently pure to meet Federal Food and Drug Administration purity standards. If the product in question is other than an end use pharmaceutical, the product is considered "pure" if it meets the relevant industry standard for purity. Such industry standards include standards, such as "Reagent Grade", etc.

Compounds that can benefit from the present invention include, but are not limited to, pharmaceutically active compounds, veterinary compounds, food materials, dyes, household and industrial chemicals, etc. Selected, non-limiting, representative compounds include hydrophilic materials as well as hydrophobic/lipophilic materials. Various hydrates and solvates in various polymorphic forms of such materials are also suitable. Conversion from hydrophilic to hydrophobic materials may often be accomplished by a pH change between a charged species and an uncharged one, such as for example conversion between a free acid or base (less water soluble) and a salt thereof (more water soluble). If the solubility shifts sufficiently, the solvents/co-solvents for one form can become the anti-solvent for the other form and the anti-solvents for the first form can become the solvents for the latter. Thus, the invention is applicable to free acids, free bases, their salts, and zwitterionic species where appropriate, and those materials having a permanent charge such as betains and sultanes, and other quaternium compounds. A general guideline as to the hydrophilic vs hydrophobic nature of compounds can be gleaned from a variety of methods known in the art. A simple system is the simple solubility of the compound in question in water and is designated by the terms "very soluble" (1 part solute/less than 1 part water), "freely soluble" (1 part solute/1 part water to 1 part solute/10 parts water); "soluble" 1 part solute/10 parts water to 1 part solute/30 parts water); "sparingly soluble" (1 part solute/30 parts water to 1 part solute/100 parts water); "slightly soluble" (1 part solute/100 parts water to 1 part solute/1000 parts water); "very slightly soluble" (1 part solute/1000 parts water to 1 part solute/10000 parts water); and "practically insoluble" or "insoluble" (1 part solute/>10000 parts water). All of the designations "very soluble", "freely soluble", "soluble", "sparingly soluble" and "slightly soluble" indicate materials which can be considered hydrophilic for the present invention. The designations "very slightly soluble", "practically insoluble", and "insoluble" can be considered hydrophobic for purposes of the invention. The above classification system is used detailed in Remington: The Science and Practice of Pharmacy 19$^{th}$ Ed., Mack Publishing co., Easton, Pa. 1995, Page 195, and is described in the United States Pharmacopoeia. A second system is by a determination of the partition coefficient, P, defined as the ratio of the concentration of a material in octanol to the concentration in water in an octanol/water system at equilibrium at 25° C. Generally, values for P are given as log P (see Handbook of Chemistry and Physics 86$^{th}$ Ed. 2005-2006 at Pages 16-41 to 16-45 and Remington: The Science and Practice of Pharmacy 19$^{th}$ Ed., Mack Publishing Co., Easton, Pa. 1995, Pages 158-159). Values of $P \ll 1$ (log P is negative) are clearly hydrophilic. Values of $P \gg 1$ are generally hydrophobic. However, since this measure is in the octanol/water system, it is not absolutely controlling in the invention, but merely indicative of whether a particular material is a likely hydrophilic or likely hydrophobic one for initial consideration of the solvent, co-solvent, and anti-solvent to use. Another guideline useful for consideration of the hydrophilic or hydrophobic nature of the material is the hydrophilic-lipophilic balance (HLB) system. (See Remington above, pages 287-288). Although the HLB system was developed for surface active agents, it does give another guideline as to the hydrophilic nature or hydrophobic nature of a material, with hydrophilic materials having an HLB greater than about 10 and hydrophobic materials having an HLB value generally below about 10. Once a potential solvent and potential anti-solvent are selected however, confirmation should be sought that the chosen anti-solvent does substantially push the material out of solution in the chosen solvent or solvent/co-solvent mixture. The more efficiently and completely the anti-solvent pushes the material out of solution, the better the invention should be expected to give the desired results.

Useful compounds which can be prepared in lyophilizate form according to the invention (generally include, but are not limited to, end use acceptable salts, amides thereof, sulfonamides thereof, carbamates thereof, esters thereof and phosphoesters thereof, hydrates and solvates thereof, and crystalline polymorphs and amorphous forms thereof, and racemates, enantiomers, and diastereomers thereof). In the following exemplary list, most of the compounds are pharmaceutically or veterinary acceptable compounds. Thus, the salt or ester is preferably those that are acceptable in these uses. However, if the lyophilizate will be further modified before being used as a pharmaceutical or veterinary material, the salt or ester is not so limited. In addition, the following more extensive list, lists one moiety for the free base, the free acid, and all salts thereof, so that the absence of a particular salt or of the free acid or free base when another is present, should be construed to include the listing of all such suitable forms. Similarly, not all pharmaceutically acceptable esters are indicated, and again, the listing of a non-esterified form should be deemed to include the suitable esterified counterparts. In addition, compounds having a quaternary ammonium are listed only as the primary species without reference to the counterion (i.e., benzalkonium, rather than benzalkonium chloride, etc), but all suitable counterions are deemed to be within the scope of the invention.

In light of the size of the more extensive list, the inventor presents his preferred compounds of interest, but this is only in the interest of clarity and should not be taken as a limitation on the broader scope of the invention. Preferred compounds for use as the material to be lyophilized according to the invention include antibiotics (including penicillins, cephalosporins, tetracyclines, macrolides, etc) xanthines, anesthetics (including barbiturates, narcotics, and the "caines"), antiemetics, anti-cancer agents, etc. A specifically preferred group of compounds includes, but is not limited to, alfentanil (particularly the hydrochloride especially the monohydrate), amifostine (particularly the amorphous and trihydrate forms), aminophyllin (particularly the dehydrate form), amoxicillin (particularly the trihydrate form), ampicillin (especially the trihydrate form), bupivacaine (especially the hydrochloride salt and particularly the monohydrate form), caffeine (especially the monohydrate form), cefepime (especially the hydrochloride salt and particularly the monohydrate form), ceftazidime (especially the pentahydrate form), ceftriaxone (especially the 3.5 hydrate form), cephradine (particularly the mono and di hydrate forms), chromic chloride (especially the hexahydrate form), clindamycin (especially the monohydrate form), codeine, cyclophosphamide, cysteine, dextrose, doxapram (particularly the hydrochloride salt and especially the monohydrate form) doxycycline (especially the monohydrate form), edetate (especially the dihydrate form), hyoscyamine (especially the sulfate salt and the dihydrate form), levorphanol (especially as the dihydrate form), lidocaine (particularly as the hydrochloride salt and especially as the monohydrate form), lincomycin (particularly as the hydrochloride salt and especially in the monohydrate form), menadiol (particularly as the sodium diphosphate salt and especially in the hexhydrate form), neropenam (especially as the trihydrate), metoclopramide (particularly as the hydrochloride salt and especially in the monohydrate form), morphine (particularly as the sulfate salt and especially in the pentahydrate form), nafcillin (particularly as the sodium salt and especially in the monohydrate form), norepinephrine (particularly as the bitartrate salt and especially in the monohydrate form), ondansetron (particularly as the hydrochloride salt and especially in the dihydrate form), oxacillin (particularly as the sodium salt and especially as the monohydrate), oxytetracycline (especially as the dihydrate), piperacillin (especially as the monohydrate, scopolamine (particularly as the hydrobromide salt and especially as trihydrate), spectinomycin (particularly as the dihydrochloride and especially as the pentahydrate), succinylcholine (particularly as the chloride salt), theophylline (especially as the monohydrate), thiothixene (particularly as the dihydrochloride and especially as the dihydrate), tubocurarine (particularly as the hydrochloride salt and especially as the pentahydrate form), moxifloxacin, tacrolimus, itraconazole, argatroban, posaconazole, voraconazole, docetaxel, fludarabine, glatiramer acetate, gemcitabine, irinotecan, epoprostenol, and 7-ethyl-10-hydroxy camptothecin.

A more complete list of compounds, most of which are pharmaceutical or veterinary, which can be utilized in the present invention includes, but is not limited to: abacavir, abamectin, abanoquil, abaperidone, abarelix, abecamil, abiraterone, abitesartan, ablukast, abunidazole, acadesine, acamprosate, acaprazine, acebrochol, acebutolol, acecainide, acecarbromal, aceclidine, aceclofenac, acedapsone, acediasulfone, acedoben, acefluranol, acefurtiamine, acefylline clofibrol, acefylline piperazine, aceglatone, aceglutamide, acemetacin, aceneuramicacid, acenocoumarol, acepeprone, acepromazine, aceprometazine, acequinoline, acesulfame, acetaminosalol, acetanilide, acetarsone, acetaminophen, acetazolamide, acetiamine, acetiromate, acetohexamide, acetophenazone, acetophenetidin, acetorphine, acetosulfone, acetriozoic acid, acetylcysteine, acetyldigitoxin, acetylleucine, acetyltributyl citrate, acetyltriethyl citrate, acevaltrate, acexamin acid, acifran, acipimox, acitazanolast, acitemate, acitretin, acivicin, alcantate, aclarubicin, aclatonium napadisilate, acolbifene, aconiazide, aconitine, acotiamide, acoxatrine, acreozast, acridorex, acriflavine, acrihellin, acrisorcin, acrivastine, acroinonide, acronine, actaplanin, actarit, actinoquinol, actisolide, actodigin, acyclovir, adafenoxate, adamexine, adapalene, adaprolol, adatanserin, adefovir, adekalant, adelmidrol, ademitrionine, adenosine, adibendal, adicillin, adimolol, adinazolam, adiphenine, aditeren, aditoprim, adosopine, adozelesin, adrafinil, adrenalone, adrogolide, afalanine, afeletecan, afloqualone, afovirsen, afurolol, aganodine, aglepristone, agomelatine, aklomide, alacepril, alafosfalin, alagebrium, alamecin, alamifovir, alanine, alanosine, alaproclate, alatrofloxacin, alazanine triclofenate, albaconazole, albendazole, albuterol, albutoin, alclofenac, alclometasone, alcloxa, alcuronium, aldioxa, aldosterone, alemcinal, alendronic acid, alentemol, alepride, alestramustine, aletamine, alexidine, alexitol, alexomycin, alfacalcidol, alfadex, alfidalone, alfaprostol, alfatradiol, aldaxalone, alfentranil, alfluzosin, algeldrate, algestone, alibendol, aliconazole, alifedrine, alifurane, alilusem, alimadol, alinastine, alinidine, alipaminde, aliskiren, alitame, alitretinoin, alizapride, alletorphine, allobarbitol, allocamide, allocupreide, allomethadione, allopurinol, allylestrenol, allylprodine, almecillin, almestrone, alminoprofen, almitrine, almokalant, almotriptan, almoxatone, almurtide, alnespirone, alniditan, alonacic acid, alonimid, aloracetam, alosetron, alovudine, aloxidone, aloxiprin, aloxistatin, alozafone, alpertine, alphameprodine, alphamethadol, alphamethyldopa, alphaprodine, alpidem, alpiropride, alprafenone, alprazolam, alprenolol, alprenoxime, alprostadil, alrestatin, altanserin, altapizone, alteconazole, althiazide, altinicline, altoqualiine, altrenogast, altretamine, alvemeline, alverine, alvimopan, alvocidib, amadinone, amafalone, amanozine, amantadine, amantocillin, ambamustine, ambasilide, ambazone, ambenonium, ambenoxan, ambomycin, ambrisentan, ambroxol, ambruticin, ambucaine, ambucetamide, ambuphylline, ambuside, ambutonium, amcinafal, amcinafide, amcinonide, amdinocillin, amdoxovir, ambucort, amedalin, amelometasone, ameltolide, amelubant, amesergide, ametantrone, amethocaine, amezapine, amezinium, amfenac, amfepentorex, amfetaminil, amflutizole, amfonelic, amicarbalide, amicloral, amicycline, anidantel, amidapsone, amidephrine, amiflamine, amifloverine, amifloxacin, amifostine, amiglumide, amikacin, amikhelline, amiloride, amiloxate, aminacrine, amindocate, amineptine, aminoglutethimide, aminohippuric acid, aminolevulinic acid, aminometradine, aminopentamide, aminophenazone, aminophylline, aminopromazine, aminopterin, aminopyrine, aminoquinol, aminoquinuride, aminorex, aminosalicylic acid, aminothiazole, amiodarone, amiperone, amphenazole, amipizone, amiprolose, amiquinsin, amisometradine, amisulprode, amiterol, amithiozone, amitivir, amitraz, amitriptyline, amitriptyinoxide, amixetrine, amlexanox, amlintide, amlodipine, amocarzine, amodiaquine, amolanone, amonafide, amoproxan, amopyroquine, amorolfine, amoscanate, amosulatol, amotosalen, amotriphene, amoxapine, amoxecaine, amoxicillin, amoxydramine, amperozide, anphechloral, amphenidone, amphetamine, amphomycin, amphotalide, amphotericin, ampicillin, ampiroxicam, amprenavir, amprolium, ampyrimine, ampyzine, amquinate, amrubicin, amsacrine. amtolmetin, amustaline, amylobarbital, angestone, anagrelide, anakinra, anaritide, anastrozole, anatibant, anaxirone, anazocine, anazolene, ancarolol, ancitabine, andolast, androstenediol, androstenedione, andulafungin, anecortave, anetholtrithion, angiotensin amide, andidoxamine, anidulafungin, anilamate, anileridine, anilopam, anipamil, aniracetam, anirolate, anisacril, anisindione, anisopirol, anisotropine, anisperimus, anitrazafen, anpirtoline, ansoxetine, antafenite, antazoline, antazonite, anthelmycin, anthralin, anthramycin, antipyrine, antrafenine, apadoline, apafant, apalcillin, apaxafylline, apaziquone, apazone, apicycline, aplindore, apomorphine, apovincamine, apraclonidine, apramycin, aprepitant, aprakalim, aprindine, aprinocarsine, apofene, aprosulate, aptazapine, aptiganel, aptocaine, aranidipine, aranotin, arbaprosil, arbekacin, arbutamine, arclofenin, ardacin, ardeparin, arecoline, arfalasin, arfendazam, arformoterol, argatroban, argimesna, argipressin, argiprestocin, arlidone, arimoclomol, aripiprazole, armodafinil, arnolol, arofylline, artinolol, arprinocid, arpromidine, arsanilic acid, arteflene, artemether, artemisinin, artemotil, artenimol, artesunate, articaine, artilide, arundic acid, arzoxifene, ascorbic acid, arsenapine, aseripide, asimadoline, asobamast, asocainol, asoprisnil, aspartame, aspartocin, asperlin, aspirin, aspoxicillin, astemizole, astromicin, asulacrine, atamestane, ataprost, ataquimast, atavanavir, atenolol, atevirdine, atibeprone, atilmotin, atipamezole, atipromod, atiprosin, atizoram, atliprofen, atocalcitol, atolide, atomoxetine, atorvastatin, atosiban, atovaquone, atracurium, atrasentan, atraleuton, atrimustine, atrinositol, atromepane, atropine, atropine oxide, auranofin, aurothioglucose, avanafil, avasimibe, avicatonin, avalamycin, aviptadil, avitriptan, avizafone, avobenzone, azoparcin, avorelin, avridine, axamozide, axitirome, axomadol, azabon, azabuperone, azacitidine, azacitidine, azaclorzine, azaconazole, azacosrterol, azacyclonol, azaftozine, azalanstat, azalomycin, azaloxan, azamethiphos, azamethonium, azamulin, azanator, azanidazole, azaperone, azapetine, azaquinzole, azaribine, azarole, azaserine, azasetron, azaspirium, azastene, azatadine, azathioprine, azelaic acid, azelastine, azelinnidipine, azepexole, azepindole, azetepa, azetirelin, azidamfenicol, azidocillin, azimexon, azimilide, azintamide, azipramide, azithromycin, azlocillin, azlocillin, azolimine, azosemide, aztomycin, aztreonam, azumolene, bacampicillin, bacitracin, baclofen, bacmecillinam, bakeprofen, balaglitazone, balazipone, balofloxacin, balsalazide, bamaluzole, bamaquimast, bambermycin, bambuterol, bamethan, bamifylline, bamipine, bamirastine, bamidazole, banoxantrone, baquilopirm, barbexaclone, barbital, barixibat, barmastine, barnidipine, barucainide, barusiban, basifungin, batalbulin, batanopride, batebulast, batelapine, batilol, batimastat, batoprozine, baxitoizine, bazedoxifene, bazinaprine, becanthone, becatecarin, beciparcil, beclamide, becliconazole, beclobrate, beclomethasone, beclotiamine, befetupitant, befiperide, befloxatone, befunolol, befuraline, bekanamycin, belaperidone, belarizine, belfosdil, belotecan, beloxamide, beloxepin, bemarinone, bemegride, bemesetron, bemetizide, beminafil, bemiparin, bemetradine, bemoradan, bemotrizinol, benactyzine, benafentrine, benapryzine, benaxibine, benazepril, bencianol, bencisteine, benclonidine, bencyclane, bendacalol, bendamustine, bendazac, bendazol, benderizine, bendroflumethazide, benethamine penicillin, benexate, benfluorex, benfosformin, benfotiamine, benflurodil, benhepazone, benidipine, benmoxin, benolizime, benorilate, benorterone, benoxifos, benoxaprofen, benoxinate, benpenolisin, benperidol, benproperine, benrixate, bensalan, benserazide, bensuldazic acid, bentazepam, bentemazole, bentiamine, bentipimine, bentiromide, bentoquatam, benurestat, benzalkonium, benzarone, benzbromarone, benzestrol, benzethidine, benzethonium, benzetimide, benzilonium, benzindopyrine, benziodarone, benzmalecene, benznidazole, benzobarbital, benzocaine, benzoclidine, benzoctamine, benzodepa, benzododecinium, benzonatate, benzopyrronium, benzoquinonium, benzotript, benzoxiquine, benzoxonium, benzoylpas, benzphetamine, benzpiperylon, benzpyrinium, benzquercin, benzquinamide, benzthiazide, benztropine, benzydamine, benzylhydrochlorothiazide, benzylpenicillin, benzylsulfamide, bepafant, beperidium, bephenium, bepiastine, bepridil, beractant, beraprost, berberine, berefrine, bergenin, berlafenone, bermoprofen, bertosamil, berupipam, bervastatin, berythromycin, besigomsin, besipirdine, besonprodil, besulpamide, besunide, beta carotene, betacetylmethadol, betahistine, betaine, betameprodine, betamethadol, betamethasone, betamicin, betamipron, betaprodine, betaxolol, betazole, bethanacol, bethanidine, betiatide, betoxycaine, bevantolol, bevonium, bexarotene, bexlosteride, bezafibrate, beztiramide, bialamicol, biapenem, bibezonium, bibrocathol, bilcalutamide, bicifadine, bicoldil, biclofibrate, biclotymol, bicozamycin, bidimazium, bidisomide, bietamiverine, bietaserpine, bifemelane, bifepramide, bifeprofen, bifeprunox, bifluranol, bifonazole, bilastine, bimakalim, bimatoprost, bimoclomol, bimosiamose, bindarit, binedaline, binfloxacin, binfibrate, biniramycin, binizolast, binodenosine, binospirone, bioallethrin, botin, bipenamol, biperiden, biphenamine, biricodar, biriperone, bisacodyl, bisantrene, bisaramil, bisbendazole, bisbentiamine, bisbutiamine, bisdequilinium, bisfenazone, bisfentidine, bisnafide, bisorbin, bisoctriazole, bisoprolol, bisorcic, bisoxatin, bispyrithione, bithonol, bithionoloxide, butipazone, bitolterol, bitoscanate, bivalirudin, bizelesin, bleomycin, blonanserine, bluensomycin, bofumustine, bolandiol, bolasterone, bolazine, boldenone, bolenol, bolmantalate, bometolol, bopindolol, bornaprine, bornaprolol, borelone, borocaptane, bortezomib, bosentan, botiacrine, boxidine, brallobarbital, brasofensine, brazergoline, brefonalol, bremazocine, brequinar, bretazenil, bretyllium, brifentanil, brimonidine, brinazaprone, brindoxime, brinzolamide, brivudine, brobactam, broclepride, brocrestine, brocrinat, brodimoprim, brofaromine, brofoxine, brolaconazole, brolamfetamine, bromadoline, bromamid, bromazepam, bromchlorenone, bromebric acid, bromerguride, brometenamine, bromfenac, bromhexene, bomindione, bromisovalum, bromociclen, bromocriptine, bromodiphenylhydramine, bromofenfos, bromofos, bromopride, bromoxanide, bromperidol, brompheniramine, broparestrol, broperamol, bropirimine, broquinaldol, brosotamide, brostallicin, brosuximide, brotianide, brotizolam, brovanexine, brovincamine, broxaldine, broxaterol, broxitalamide, broxuridine, broxyquinoline, bucainide, bucetin, buciclovir, bucillamine, bucindolol, bucladesine, buclizine, buclosaminde, bucloxic acid, bucolme, bucricaine, bucromarone, bucumolol, budesonide, budipine, budotitane, budralazine, bufenadrine, bufeniode, bufetolol, bufexamac, bufezolac, buflomedil, bufogentin, buformin, bufrolin, bufuralol, bufylline, bulaquine, bumadizone, bumecaine, bumepidil, bumetanide, bumetriazole, bunaftine, bunamidine, bunamiodyl, bunaprolast, bunazosin, bunitrolol, bunolol, buparvaquone, bupicomide, bupivacaine, bupranolol, buprenorphine, bupropion, buquinerin, buquinolate, buquiterine, buramate, burodiline, buserelin, buspirone, busulfan, butobarbital, butacaine, butacetin, butaclamol, butadiazamide, butafosfan, butalamine, butalbital, butamben, butamirate, butamisole, butamoxane, butanilicaine, butanserin, butantrone, butaperazine, butaprost, butaverine, butedronate, bytenafine, buterizine, butenamate, buthiazide, butibufen, butifrine, butikacin, butilfenin, butinazocine, butinoline, butirosin, butixirate, butixocort, butobendine, butoconazole, butocrolol, butoctamide, butofiolol, butonate, butopamine, butopiprine, butoprozine, butopyrammonium, butorphanol, butoxamine, butoxylate, butriptyline, butropium, butylscopolamine, butynamine, buzepide, cabastine, cabergoline, cactinomycin, cadralazine, cadrofloxacin, cafaminol, cafedrine, caffeine, calcifediol, calciprotriene, calcitriol, calcobutrol, caldaret, caldiamine, caloxetic acid, calteridol, clausterone, camazepam, cambendazole, camaglibose, camiverine, camptothecin and its analogues such as 9-amino camptothecin, 10-hydroxy camptothecin, 7-ethyl-10-hydroxy camptothecin, 9-nitro camptothecin and all other camptothecin analogues with six, seven and eight membered lactone rings, camonagrel, camostat, camylofin, canbisol, candesartan, candicidin, candocuronium, candoxatril, candoxatrilat, canertinib, canfosfamide, cangrelor, cannabinol, canrenoate, canrenone, capectitabine, capobenate, capobenic acid, capravirine, capreomycin, capromorelin, caproxamine, capsaicin, captamine, captodiame, captopril, capuride, carabersat, caracemide, carafiban, caramiphen, carbachol, carbadox, carbamazepine, carbentel, carbasone, carbaspirin, carbazeran, carbazochrome, carbazocine, cabenicillin, carbenoxolone, carbenzide, carbetapentane, carbetocin, carbidopa, carbimazole, carbinoxamine, carbiphene, carbofenotion, carboplatin, carboprost, carboquone, carbubarb, carburazepam, carbutamide, carbuterol, carcainium, carebastine, carfentanil, carfimate, cargutocin, cariporide, carisoprodol, carmantadine, carmofur, carmoterol, carmustine, carnidazole, carnitine, carocainide, caroverine, caroxazone, carperidine, carperitide, carperone, carphenazine, carpindolol, carpipramine, carprazidil, carprofen, capronium, carsalam, carsatrin, cartasteine, cartazolate, carteolol, carubicin, carumonam, carvedilol, carvotroline, carzelesin, carzenide, casanthranol, casokefaminde, caspofungin, cathine, cathinone, cebaracetam, cedefingol, cefaclor, cefadroxil, cefalonium, cefaloram, cefamandole, cefaparole, cefatriazine, cefazaflur, cefazedone, cefazolin, cefbuperazone, cefanel, cefcapene, cefclidin, cefdaloxime, cefdinir, cefditoren, cefedrolor, cefempidone, cefepime, cefetamet, cefetecol, cefetriaole, cefivtril, cefixime, cefmatilen, cefmenoxine, cefmepidium, cefmetazole, ceminox, cefodizime, cefonicid, cefoperazone, ceforanide, cefoselis, cefotaxime, cefotetan, cefotiam, cefovecin, cefoxazole, cofoxitin, cefozopran, cefpimizole, cefpiramide, cefpodoxime, cefprozil, cefquinome, cefrotil, cefroxadine, cefsulodin, cefsumide, ceftazidime, cefteram, ceftezole, ceftibuten, ceftioflur, ceftiolene, ceftioxide, ceftioxime, ceftriaxone, cefuracetamime, cefuroxime, cefuzonam, celecoxib, celgosivir, celiprolol, cemadotin, cephacetrile, cephadrine, cephalexin, cephaloglycin. Cephaloridine, cephalothin, cephapirin, cepharanthine, cephradine, cericlamine, cerivastatin, ceronapril, ceruletide, cetaben, cetalkonium, cetamolol, cetefloxacin, cethexonium, cethromycin, cetiedil, cetilistat, cetirizine, cetocycline, cetopheincol, cetotiamine, cetoxime, cetraxate, cetrimonium, cetylpyridinium, cevimeline, chaulmosulfone, chenodiol, chinofon, chlofibrate, chlophendianol, chloracyzine, chloralose, chlorambusil, chloramines-T, chloramphenicol, chlorazanil, chlorbenoxamine, chlorbetamide, chlorcyclizine, chlordantoin, chlordiazepoxide, chlordimorine, chlorhexidine, chlorindanol, chlorisondamine, chloramadione, chlormerodrin, chlormezanone, chlormidazole, chlornaphazine, chloroazodin, chloroprednisone, chloroprocaine, chloropyramine, chloroquine, chloroserpidine, chlorothen, chlorothiazide, chlorotrianisene, chloroxine, chloroxylenol, chlorphenesin, chlorpheniramine, chlorphenoctium, chlorphenoxamine, chlorphentermine, chlorproethazine, chlorproguanil, chlorpromazine, chlorpropamide, chlorprothixene, chlorpyrifos, chlortetracycline, chlorthalidone, chlorthenoxazine, chlorzoxazone, cholecalciferol, cholesterol, choline alfoscerate, choline, chromic chloride, chromonar, ciadox, ciaftalan, ciamexon, cianergoline, cianidanol, cianopramine, ciapilome, cicaprost, cicarperone, ciclactate, ciclafrine, ciclazindol, ciclesonide, clcletanine, cicliomenol, ciclonicate, ciclonium, ciclopirox, ciclopramine, cicloprofen, cicloprolol, ciclosidomine, ciclotizolam, ciclotropium, cicloxilic acid, cicloxolone, cicortonide, cidofovir, cidoxepin, cifenline, cifostodine, ciglitazone, ciheptolane, ciladopa, cilansertron, cilastatin, cilazapril, cilengitide, cilexin, cilnidipine, cilobamine, cilobradine, cilofungin, cilomilast, cilostamide, cilostazol, ciluprevir, cilutazoline, cimaterol, cimemoxin, cimetidine, cimetropium, cimicoxib, cimoxatone, cinacalcet, cinalukast, cinametic acid, cinamolol, cinanserin, cinaproxen, cinchophen, cinecromen, cinepazet, cinepazide, cinfenine, cinfenoac, cinflumide, cingestol, cinitapride, cinmetacin, cinnamaverine, cinnamedrine, cinnarizine, cinnofuradione, cinoctramide, cinodine, cinolazepam, cinoquidox, cinoxacin, cinoxate, cinoxolone, cinoxopazide, cinperene, cinprazole, cinpropazide, cinpromide, cintazone, cintriamide, cinuperone, cioteronel, cipamfylline, cipemastat, ciprafamide, cipralisant, ciprazafone, ciprefadol, ciprocinonide, ciprofibrate, ciprofloxacin, ciprokiren, cipropride, ciproquazone, ciprestene, ciramadol, cirazoline, cirolemycin, cisapride, cisatracurium, cinconazole, cismadinone, cisplatin, cistinexine, citalopram, citatepine, citenamide, citenazone, citicoline, citiolone, cizolirtine, cladribine, clamidoxic acid, clamikalant, clamoxyquin, clanfenur, clanobutin, clantifen, clarithromycin, clavulanate, clazolam, clazolimine, clazuril, clebopride, clefamide, clemastine, clemeprol, clemizole, clenbuterol, clenpirin, clentiazem, cletoquine, clevidipine, clevudine, clibucaine, clidafidine, clidanac, clindium, climazolam, climbazole, climiqualine, clinafloxacin, clindamycin, clinofibrate, clinolamide, clinprost, clioquinol, clioxanide, cliprofen, cliropamine, clobazam, clobenoside, clobenzepam, clobenorex, clobenztropine, clobetasol, clobetasone, clobutinol, clobuzarit, clocanfamide, clocapramine, clociguanil, clocinizine, clocortolone, clocoumarol, clodacaine, clodanolene, clodazon, clodoxopone, clodronate, clofarabine, clofazimine, clofenamic acid, clofeniclan, clofenetamine, clofenoxyde, clofevine, clofexamine, clofezone, clofibrate, clofibric acid, clofibride, clofilium, clofucarba, clofoctol, cloforex, clofurac, clogestone, cloguanamil, clomacrin, clomegestone, clometacin, clometherone, clomethiazole, clometocillin, clomifenoxide, clominorex, clomiphene, clomipramine, clomocycline, clomoxir, clonazepam, clonazoline, clonidine, clonitazine, clonixeril, clonixin, clopamide, clopenthixol, cloperastine, cloperidone, clopidogrel, clopidol, clopimozide, clopipazan, clopirac, cloponone, cloprendol, cloprostenol, cloprothiazole, cloquinate, cloquinozine, cloracetadol, cloranolol, clorazepate, clorazepic acid, clorethane, chlorexolone, clorfenvinos, clorgiline, cloricromen, cloridarol, clorindanic acid, clorindione, clormecaine, cloroperone, clorophene, cloroqualone, clorotepine, clorprenaline, clorsulon, clortermine, closantel, closiramine, clostebol, clothiapine, clothixamide, clotiazepam, cloticasone, clotioxone, clotixamide, clotrimazole, clovoxamine, cloxacepride, cloxacillin, cloxazolam, cloxestradiol, cloximate, cloxotestosterone, cloxypendyl, cloxyquin, clozapine, cobalamide, cocaine, codeine, codoxime, cofistatin, cogazocine, colchicines, colestolone, colfenamate, colforsin, colfosceril, colimecycline, colterol, coluracetam, conessine, congazone, conivaptan, conorphone, cormethasone, corticorelin, cortisone, cortisuzol, cortivazol, cortodoxone, cotinine, cotriptyline, coumaphos, coumazolin, coumermycin, coumetarol, creatinine, creatinolfosfate, cresotamide, cridanimod, crilvastin, crisnatol, crobenetine, croconazole, cromakalim, cromitrile, cromoglicate lisetil, cromolyn, crolom, cronidipine, cropropamide, crotamiton, crotetamide, crotoniazide, crotoxyfos, crufomate, cuprimyxin, cuproxoline, cyacetacide, cyamemazine, cyanocobalamine, cyclacillin, cyclamate, cyclamic acid, cyclandelate, cyclarbamate, cyclazocine, cyclazodone, cyclexanone, cyclindole, cycliramine, cyclizine, cyclobarbital, cyclobendazole, cyclobenzaprine, cyclobutoic acid, cyclobutyrol, cyclocumarol, cyclofenil, cycloguanil, cycloheximide, cyclomenol, cyclomethycaine, cyclopentamine, cyclopenthiazide, cyclopentolate, cyclophenazine, cyclophosphamide, cyclopregnol, cyclopyrronium, cycloserine, cyclothiazide, cyclovalone, cycotiamine, cycrimine, cyfluthrin, cyhalothrin, cyheptamide, cyheptropine, cynarine, cypenamine, cypermethrin, cypothrin, cyprazepam, cyprenorphine, cyprodenate, cyproheptadine, cyprolidol, cyproquinate, cyproterone, cyproximide, cyromazine, cysteamine, cysteine, cystine, cytarabine, cythiolate, dabelotine, dabigatran, dabuzalgron, dacarbazine, dacemazine, dacinostat, dacisteine, dacopafant, dactinomycin, dacuronium, dagapamil, dagluril, dalbavancin, dalbraminol, dalcotidine, daledalin, dalfopristin, dalteparin, daltroban, dalvastatin, dametralast, damotepine, danazol, daniquidone, danittracen, danofloxacin, danosteine, danthron, dantrolene, dapiprazole, dapitant, dapivirine, dapoxetine, dapsone, daptomycin, darbufelone, darenzepine, darglitazone, darifenacin, darodipine, darunavir, darusentan, dasantafil, dateliptium, daunorubicin, daxalipram, dazadrol, dazepinil, dazidamine, dazmegrel, dazolicine, dazopride, dazoquinast, dazoxiben, deboxamet, debrisoquin, decamethonium, decimemide, decitabine, decitropine, declenperone, declopramide, decloxizine, decominol, decoquinate, dectaflur, deditonium, deferasirox, deferiprone, deferoxamine, deflazacort, defosfamine, defoslimod, degarelix, dehydroacetic acid, dehydrocholic acid, dehydroemetine, delanterone, delapril, delavirdine, delquamine, deergotrile, delfantrine, delfaprazine, selmadinone, delmetacin, delmpinol, delorazepam, deloxolone, delprostenate, delucemine, dembrexine, demecarium, demeclocycline, demecolcine, demecycline, demegestone, demelverine, demexiptiline, democonazole, demoxepam, demoxytocin, denatonium, denaverine, denbufylline, denipride, denofungin, denopamine, denotivir, denpidazone, denufosol, denzimol, depelestat, depramine, depreotide, deprodone, deprostil, deptropine, dequalinium, deracoxib, deramciclane, deriglidole, derpanicaine, dersalazine, desapidin, desciclovir, descinolone, deserpidine, desipramine, deeslanoside, desloratidine, deslorelin, desmeninol, desmethylmoramide, desmopressin, desocriptine, desogestrel, desmorphine, desonide, desoximetasone, desoxycorticosterone, desvenlafaxine, detajmium, detanosal, deterenol, detirelix, deticiclovir, detromidine, detorubicin, detrothyronine, devapamil, devazepide, dexamethasone, dexamisole, dexbrompheniramine, dexbudesonide, dexchlorpheniramine, dexclamol, dexecadotril, dexefaroxan, dexetimide, dexetozoline, dexfenfluramine, dexfosfoserine, dexibuprofen, deximafen, dexindoprofen, dexivacaine, dexketoprofen, dexlofexidine, dexloxiglumide, dexmedetomidine, dexmethylphenidate, dexnafenodonee, dexniguldipine, dexnorgestrel, dexormaplatin, dexoxadrol, dexpanthenol, dexpemedolac, dexpropranolol, dexproxibutene, dexrazoxane, dexsecoverine, dexsotalol, dextilidine, dextiopronin, dextofisopam, dextroamphetamine, dextrofemine, dextromethorphan, dextromoramide, dextrorphan, dextrothyroxine, dexcerapimil, sezaguanine, dezinamide, dezocine, diacerein, diacetamate, diacetolol, diamfenetide, diamocaine, diampromide, diamthiazole, diapamide, diarbarone, diathymosulfone, diatrizoate, diaveridine, diazepam, diaziquone, diazoxide, dibekacin, dibemethine, dibenzepin, dibenzothiophene, dibrompropamidine, bibromsalan, dibrospidium, dibucaine, dibuprol, dibupyrone, dibusadol, dicarbine, dicarfen, dichloralphenazone, dichloramine, dichlorisone, dichlormezanone, dichlorophen, dichlorphenarsine, dichloroxylenol, dichlorphenamide, dichlovos, diciferron, dicirenone, diclazuril, diclofenac, diclofenamide, diclofensine, diclofutrime, diclometide, diclonixin, diclorafurea, dicloxacillin, diclolinium, dicumrol, dicyclomine, didanosine, didrovaltrate, dieldrin, dienestrol, dienogest, diethadione, diethylphthalate, diethylcarbamazine, dietylpropion, diethylstilbestrol, dethylthambutene, dietyltoluamide, dietifen, difebarbamate, difemerine, difemetorex, difenamizole, difencloxazine, difenoximide, difenoxin, difetarsone, difeterol, diflomotecan, diflorasone, difloxacin, difluanine, diflucortolone, diflumidone, diflunisal, difluprednate, diftalone, digitalis, digitoxin, digoxin, dihexyverine, dihydralazine, dihydrocodeine, dihydroergotamine, dihydrostreptomycin, dihydrotachysterol, diisobutylaminobenzoyloxypropyl theophylline, diisopromine, diisopropanolamine, diisopropylamine, dilazep, dilevalol, dilmefone, diloxanide, diltiazem, dimabefylline, dimadectin, dimecamine, dimeclonium, dimecrotic acid, dimefadane, dimefline, dimelazine, dimenhydrinate, dimenoxadol, dimepheptanol, dimepranol, dimepregnen, dimepropion, dimeprozan, dimesna, dimesone, dimetacrine, dimetamfetamine, dimethadione, dimethazan, dimethisoquin, dimethisterone, dimetholizine, dimethothizine, dimethoxanate, dimethylaminoethyl reserpilinate, dimethylthambutene, dimethyltubocurarinium, dimetipirium, dimetofrine, dimetridazole, diminazene, dimiracetam, dimoxamine, dimoxaprost, dimoxyline, dimpylate, dinaline, dinazafone, diniprofylline, dinitolmide, dinoprost, dinoprostone, dinsed, diohippuric acid, diosmin, diotyrosine, dioxadrol, dioxamate, dioxaphetyl butyrate, dioxation, dioxethedrin, dioxifedrine, dioxybenzone, dioxyline, dipenine, diperodon, diphemanil, diphenadione, diphenan, diphenchloxazine, diphenhydramine, diphenidol, diphenoxylate, diphenylpiperidinomethyldioxolan, diphenylpyraline, diphenoxazide, dipipanone, dipiproverine, dipivefrin, diprafenone, diprenorphine, diprobutine, diprofene, diprogulic acid, diproleandomycin, diprofylline, diproqualone, diproteverine, diprotrizoate, diproxadol, dipyridamole, dipyrithione, dipyrocetyl, dipyrone, diquafosol, dirithomycin, dirlotapide, disermolide, disquonium, disobutamide, sidofenin, sdisogluside, disopyramide, disoxaril, distigmine, disufenton, disulergine, disulfamide, disulfiram, disuprazoole, ditazole, ditekiren, ditercalinium, dithiaanine, ditiocade, ditiocarb, ditiomustane, ditolamide, ditophal, divabuterol, divalproex, divaplon, dixanthogen, dizatrifone, dizcilpine, dobesilate, dobupride, dobutamide, dobutamine, docarpamine, docebenone, docetaxel, doconazole, doconexent, docosanol, docusate, dodeclonium, dodicin, dofamium, dofequidar, dofetilide, dolasetron, doliracetam, domazoline, domiodol, domiphen, domipizone, domitroban, domoprednate, domoxin, domperidone, donepezil, donetidine, donitriptan, dopamantine, dopamine, dopexamine, dopropidil, doqualast, dorampimod, doramectin, doranidazole, dorastine, soreptide, doretinel, doripenem, dorzolamide. dosergoside, dosmalfate, dotarizine, dotefonium, dothiepin, doxacurium, doxapram, doxaprost, doxazosin, doxefazepam, doxenitoin, doxepine, doxergocalciferol, doxibetasol, doxifluridine, doxofylline, doxorubicin, doxpicomine, doxycycline, doxylamine, draflazine, dramedilol, draquinolo, drazidox, dribendazolew, drimidene, drobuline, drocinonide, droclidinium, drofenine, droloxifene, drometrizole, dromostanolone, dronabinol, drinedarone, dropempine, droperidol, dropenilamine, dropropizine, drospirenone, drotaverine, drotebanol, droxacin, droxicainide, droxicam, droxidopa, droxinavir, droxypropine, duazomycin, dulofibrate, duloxetine, dulozafone, dumorelin, dumetacin, duoperone, dupracetam, dutasteride, dyclonine, dyhydrogestrone, dymanthine, dyphylline, ebalzotan, ebastine, eberconazole, ebiratide, ebrotidine, ebselen, ecabapide, ecabet, ecadotril, ecalcidene, ecamsule, ecastolol, ecenofloxacin, echothiophate, ecipramidil, eclanamine, eclazolast, ecomustine, econazole, ecopipam, ecraprost, ectylurea, edaglitazone, edaravone, edatrexate, edelfosine, edetol, edifolone, edogestrone, edonentan, edotecarin, edotreotide, edoxudine, edratide, edronocaine, edrophonium, efaproxiral, efaroxan, efavirenz, efegatran, efepristin, efetozole, efletirizine, eflornithine, efloxate, eflucimibe, elfumast, efonidipine, efrotomycin, eganoprost, eglumetad, egtazic acid, equalen, elacridar, elantrine, elanzepine, elaarofiban, elbanizine, eldacimibe, eletriptan, elfazepam, elgotipine, elinafide, eliprodil, elisartan, ellagic acid, elliptinium, elmustine, elnadipine, elopiprazole, elsamitrucin, eltanolone, eltenac, eltoprazine, elucaine, elvucitabine, elzasonan, elziverine, emakalim, emapunil, embramine, embusartan, embutramide, emedastine, emepronium, emetine, emeglitate, emilium, emiteflur, emiverine, emodepside, emopamil, emorfazone, emtricitabine, emylcamate, enadoline, enalapril, enalaprilat, enalkiren, enazadrem, enbucrilate, encainide, enciprazine, enclomiphene, encyprate, endixaprine, endomide, endralazine, endrysone, enecadin, enefexine, enestebol, enfenamic acid, enfluvirtide, englitazone, eniclobrate, enilconazole, enilospirone, eniluracil, eniporide, enisoprost, enloplatin, enocitabine, enofelast, enolicam, enoxacin, enoxamast, enoxaparin, enoximone, enoxolone, enipiprazole, enpiroline, enprazepine, enprofylline, enpromate, enprostil, enramycin, enrasentan, enrofloxacin, ensacillin, ensulizole, entacapone, entecavir, entsufon, enviomycin, enviradene, enviroxime, enzacamene, anzastaurin, epalrestat, epanolol, eperezolid, eperisone, epervudine, ephedrine, epicainide, epicillin, epicriptine, epiestriol, epimestrol, epinastine, epinephrine, epinepheryl, epipropidine, epirizole, apiroprim, epirubicin, epitetracycline, epithiazide, epitiostanol, eplerenone, elivanserin, epoprostenol, epostane, eprazinone, eprinomectin, epristeride, eprobemide, eprosartan, eprovafen, eproxindine, eprozinol, epsipranel, epaloprost, eptapirone, eptaplatin, eptastigmine, eptazocin, eptifibatide, equillin, erbulozole, erdosteine, ergocalciferol, ergonovine, ergotamine, eritoran, erizepine, erlotinib, ercainide, ersentilide, ertapenem, ertiprotafib, erythrity tetrnitrate, erythromycin, esafloxacin, esaprazole, esatenolol, escitalopram, esculamine, eseridine, esflurbiprofen, esketamine, escarbazepine, esmolol, esomeprazole, esonarimod, esorubicin, esoxybutynin, espatropate, esproquin, estazolam, estradiol, estramustine, estrazinol, estriol, estrofurate, estrone, estropipaten esupone, eszopclone, etabenzarone, etacepride, etafedrine, etafenone, etalocib, etamestrol, etaminile, etamiphylline, etamocycline, etanidazole, etanterol, etaqualone, etarotene, etasuline, etazepine, etazolate, etebenecid, eterobarb, etersalate, ethacridine, ethacrynic acid, ehtambutol, ethamivan, ethamsylate, ethaverine, ethenzameide, ethiazide, ethinamate, ethinyl estradiol, ethionamide, ethisterone, ethoheptazine, ethomoxane, ethonam, ethopabate, ethopropazine, ethosuximide, ethotoin, ethoxazene, ethoxazorutoside, ethoxzolamide, ethybenztropine, ethyl biscoumacetate, ethyl carfluzepate, ethyl cartrizoate, ethyl dibunate, ethyl dirazepate, ethyl loflazepate, ethylestrenol, ethylhydrocupreine, ethylmethylthiambutene, ethylmorphine, ethylnorepinepherine, ethylstilbamine, ethylnerone, ethylnodil, ethypicone, etibendazole, eticlopride, eticyclidine, etidocaine, etidronate, etidronic acid, etifelmine, etifenin, etifoxine, etilamfetamine, etilefrine, etilevodopa, etinidine, etipirium, etiprendol, etiproston, etiracetam, etiroxate, etisazole, etisomicin, etisulergine, etizolam, etocarlide, etocrylene, etodolac, etodroxizine, etofamide, etofenamate, etofenprox, etofibrate, etofermin, etofuradine, etofylline, etoglucid, eorolex, etolotifen, etoloxamine, etomidate, etomidoline, etomoxir, etomitazene, etonogestrel, etoperidone, etoposide, etoprindole, etoprine, etoricoxib, etorphine, etosalamide, etoxadrol, etoxeridine, etozolin, etrabamine, etravirine, etretinate, etriciguat, etryptamine, etymemazine, eucaine, eucalyptol, eugenol, euprocin, evandamine, evernimicin, everolimus, evicromil, exalamide, exametazime, examorelin, exaprolol, exatecan, exemestane, expanol, exifone, exiprofen, exisulind, ezetimibe, ezlopitant, fadolmidine, fadrozole, falecalcitriol, falintolol, falipamil, falnidamol, famciclovir, famirapinium, famotidine, famotine, fampridine, famprofazone, fampronil, fananserin, fanapanel, fandofloxacin, fandosentan, fanetizole, fantofarone, fantridone, farglitazar, fasidotril, fasiplon, fasoracetam, faudil, fazadinium, fazarabine, febantel, febarbamate, febuprol, febuverine, febuxostat, fecleminae, feclobuzone, fedotozine, fedrilate, felbamate, felbinac, felipyrine, felodipine, feloprentan, felypressin, femoxetine, fenabutene, fenacetinol, fenaclon, fenadiazole, fenaftic acid, fenalamide, femalcomine, fenamifuril, fenamole, fenaperone, fenbendazole, fenbenicillin, fenbufen, fenbutreazate, fencamfamin, fencibutirol, fenclexonium, fleclofenac, fenclonine, fenclorac, fenclozic acid, fendiline, fendizoate, fendosal, feneritrol, fenestrel, fenethazine, fenethylline, fenetradil, fenflumizole, fenfluramine, flenfluthrin, fengabine, fenharmane, fenimide, feniodium, fenipentol, fenirfibrate, fenisorex, fenitrothion, fenleuton, fenmetozole, fenmetraminde, fenobam, fenocinol, fenocitimine, fenofibrate, fenoldopam, fenoprofen, fenoterol, fenoerine, fenoxazoline, fenoxedil, fenozolone, fenpentadiol, fenperate, fenprpalone, fenpipramide, fenpiprane, fenpiverinium, fenprinast, fenproporex, fenprostalene, fenquiaone, fenretinide, fenspiride, fentanyl, fenthion, fentiazac, fenticlor, fenticonazolem, fentonium, fenvalerate, fenyripol, fepentolic acid, fepitrizol, fepradinol, feprazone, fepromide, feprosidnine, ferpifosate, fesoterodine, fetoxylate, fexicaine, fexinidazole, fexofenadine, fezatione, fezolamine, fiacitabine, fialuridine, fibracillin, fidarestat, fidexaban, fiduxosin, figopitant, filaminast, filenadol, filipin, finafloxacin, finasteride, fingolimod, fipamezole, fipexide, fipronil, firocoxib, flavamine, flavodic acid, flavodilol, flavoxate, flazalone, flecainide, flerobuterol, fleroxacin, flesinoxan, flestolol, fletazepam, flezelastine, flibanserin, flindokalner, flocalcitriol, floctafenine, flomoxef, floptopione, florantyrone, flordipine, floredil, florfenicol, florifenine, flosatidil, flosequinan, flosulide, flotrenizine, floverine, floxacillin, floxacrine, floxuridine, flucizine, flualamine, fluanisone, fluazacort, fluazuron, flubanilate, flubendazole, flubepride, flucarbril, flucetorex, flucindole, flucinprazine, flucloronide, fluconazole, flucrylate, flucytosine, fludalanine, fludarabine, fludazonium, fludeoxyglucose, fludiazepam, fludorex, fludoxopone, fludrocortisone, flufenamic acid, flufenisal, flufosal, flufylline, flugestone, fluindarol, fluindione, flumazenil, flimecinol, flumedroxone, flumequine, flumeridone, flumethasone, flumethiazole, flumetramide, flumexadol, flumezapine, fluminorex, flumizole, flumoxonide, flunamine, flunarizine, flunidazole, flunisolide, flunitrazepam, flunixin, flunoprost, flunoxaprofen, fluocinolone, fluocinonide, fluocortin butyl, fluocortolone, fluorescein, fluoresone, fluorodopa, fluorometholone, fluorosalan, fluorouracil, fluotracen, fluoxetine, fluoxymesterone, fluparoxan, flupentixol, fluperamide, fluperlapine, fluperolone, flupheazine, flupipamide, flupirtine, flupranone, fluprazine, fluprednidene, fluprednisolone, fluprofen, fluprofylline, fluproquazone, fluprostenol, fluquazone, fluradoline, flurandrenolide, flurantel, flurazepam, flurbiprofen, fluretofen, flurithromycin, flurocitabine, flurofamide, flurogestone, flusoxolol, fluspiperone, fluspirilene, flutamide, flutazolam, flutemazepam, flutiazin, fluticasone, flutizenol, flutomidate, flutonidine, flutoprazepam, flutrimazole, flutroline, flutropium, fluvastatin, fluvoxamine, fluzinamide, fluzoperine, fodipir, folic acid, fomepizole, fomidacillin, fominoben, fomiversen, fomocaine, fonazine, fondaparinux, fopirtoline, forasartan, forfenimex, formebolone, formestane, formetorex, forminitrazole, formocortal, formoterol, forodesine, foropafant, fosamprenavir, fosarilate, fosazepam, fosenazide, fosfluconazole, fosfocreatinine, fosfomycin, fosfonet, fosfosal, fosfructose, fosinopril, fosinoprilat, fosmenic acid, fosmidomycin, fosopamine, fosphenyloin, fospirate, fosquidone, fostedil, fosrtriecin, fosveset, fotemustine, fortrenamine, fozivudine, frabuprofen, fradafiban, frakefamide, framycetin, frentizole, freselestat, fronepidil, fropenem, frovatriptan, froxiprost, ftaxilide, ftivazide, ftormetazine, ftorpropazine, fubrogonium, fudosteine, fuladectin, fulvestrant, fumagillin, fumoxicillin, fungimycin, fuprazole, furacrinic acid, furafylline, furalazine, furaltadone, furaprofen, furazabol, furazolidone, furazolium, furbicillin, furcloprofen, furegrelate, furethidine, furfenorex, furidarone, furmethoxadone, furnidipine, furobufen, furodazole, furofenac, furomazine, furomine, furosemide, furostilbestrol, fursalan, fursultiamine, furterene, furtrethonium, fusafungine, fusidate, fusidic acid, fuzlocillin, gabapentin, gabapexate, gaboxadol, gacyclidine, gadobenate, gadobutrol, gadocolectic acid, gadodiamine, gadofosveset, gadomelitol, gadopenamide, gadopentetate, gadoteric acid, gadoteridol, gadoversetamide, gadoxetate, gadoxeticaicid, galamustine, galntamine, galarubicin, galasomite, galdansetron, gallamine triethiodide, gallopamil, galocitabine, galosemide, galtifenin, gamfexine, gamolenic acid, gamaxolone, ganciclovir, ganefromycin, ganglefene, ganstigmine, gantacurium, gantofiban, gapicomine, gapromidine, garenoxacin, gatifloxacin, gavestinel, geclosporin, gedocarnil, gefarnate, gefitinib, gemazocine, gemcabene, gemcadiol, gemcitabine, gemeprost, genfibtrozil, gemifloxacin, gemopatrilat, gentamicin, gepefrine, gepirone, geroquinol, gestaclone, gestadienol, gestodene, gestonorone, gestrinone, gevotroline, gimatecan, gimeracil, giparmen, giracodazole, giractide, girisopam, gitaloxin, gitoformate, glafenine, glaspimod, glatiramer acetate. glemanserin, glenvastatin, gliamilide, globotnuride, glibutimine, glicaramide, glicetanide, gliclazide, glicondamine, glidazamide, gliflumide, glimepiride, glipalamide, glipizide, gliquidone, glisamuride, glisentide, glisindamine, glisolamide, glisoxepide, gloxazone, gloximonam, glucametacin, glucosamine, gluronolactone, glucuronamide, glunicate, glyburide, glybuthiazole, glubuzole, gycopyrrolate, glycylamide, glyhexamide, glymidine, glyoctamide, glyparamide, glypinamide, glyprothiazole, glysobuzole, goralatide, goserelin, gramicidin, granisetron, grepafloxacin, griseofulvin, guabenxan, guacetisal, guafecainol, guaiactamine, guaiapate, guaietolin, guaifenesin, guaimesal, guaisteine, guaithylline, guanabenz, guanacline, guanadrel, guanazodine, guanclofine, guancydine, guanethidine, guanfacine, guanisoquin, guanoclor, guanoctine, guanoxabenz, guanoxan, guanoxyfen, gusperimus, halazepam, halazone, halcinonide, halethazole, halobetasol, halocortolone, halofantrine, halofenate, halofuginone, halometasone, halonamine, halopemide, halopenium, haloperidol, halopredone, haloprogesterone, haloprogin, haloxazolam, haloxon, haloqionol, hamycin, hedaquinium, heliomycin, hepronicate, heptabarbital, heptaverine, heptolamide, hepzidine, heroin, hetacillin, hetaflur, heteronium, hexachlorophene, hexacyclonate, hexacyprone, hexadiline, hexafluorenium, hexamethonium, hexaminolevulinate, hexapradol, hexaprofen, hexapropymate, hexasonium, hexazole, hexedine, hexestrol, hexetidine, hexobarbital, hexobendine, hexocyclium, hexoprenaline, hexopyrronium, heylcaine, histamine, histapyrrodine, histidine, homarylamine, homatropine, homidium, homochlorcyclizine, homofenazine, homopipramol, homosalate, homprenorphine, hopantenic acid, hoquizil, hycanthone, hydracarbazine, hydralazine, hydragaphen, hydrobentizide, hydrochlorothiazide, hydrocodone, hydrocortisone, hydroflumethiazide, hydromadinone, hydromorphinol, hydromorphone, hydroquinone, hydroxyindasate, hydroxyindasol, hydroxocobalamin, hydroxyamphetamine, hydroxychloroquin, hydroxydione, hydroxypethidine, hydroxyphenamate, hydroxyprocaine, hydroxyprogesterone, hydroxypyridine tartrate, hydroxystenozole, hydroxystilbamidine, hydroxytetracaine, hydroxyzine, hymecromone, hyoscyamine, ibafloxacin, ibandronate, ibazocine, ibopamine, ibrolipim, ibrotamide, ibudalast, ibufenac, ibuprofen, ibuproxam, ibutamoren, ibuterol, ibutilide, ibuverine, icaridin, icatibant, iclaprim, icazepam, icodulinium, icofungipen, ifometasone, icopezil, icosapent, icospiramide, icotidine, icrocaptide, idarubicin, idaverine, idazoxan, idebenone, idenast, idoxifene, idoxuridine, idralfidine, idramantone, idraparinux, idrapril, idremcinal, idrociliamide, idronoxil, idropranolol, iferanserin, ifetroban, ifosfamide, ifoxetine, iganidipine, igmesine, iguratimod, ilaprazole, ilatreotide, ilepcimide, iliparcil, ilmofosine, iloomastat, ilonidap, iloperidone, imafen, imanixil, imatinib, imazodan, imcarbofos, imiclopazine, imidafenacin, imidapril, imidaprilat, imidocarb, imidoline, imidurea, imiglitazar, imiloxan, iminophenimide, imipenem, imipramine, imipraminoxide, imiquimod, imirestat, imitrodast, imolamine, imoxiterol, impacarzine, implitapide, impromidine, improsulfan, imuracetam, inamirone, inaperisone, incadronic acid, indacaterol, indacrinone, indalpine, indanazoline, indanidine, indanorex, indapamide, indatraline, indecainide, indeloxazine, indenolol, indibulin, indigotindisulfonate, indinavir, indiplon, indisetron, indobufen, indocate, indocyanine green, indolapril, indolidan, indomethacin, indopanolol, indopine, indoprofen, indoramin, indorenate, indoxole, indriline, inecalcitol, ingliforib, inicarone, inocterone acetate, inogatran, inosine, inositol, improquoone, intoplicine, intrazole, intriptyline, inulin, iobenguane, iobenzamic acid, iobitridol, iobutoic acid, icanlidic acid, iocarmic acid, iocetamic acid, iodamine, iodipamide, iodixanol, iodoantipyrine, iodocholesterol, iodohippurate, iodoquinol, iodothiouracil, idoxamic acid, iofetamine, ioflupane, iofratol, ioglicic acid, ioglucol, ioglunide, ioglycamic acid, iogulaamide, iohexol, iolidonic acid, iolixanic acid, iolopride, iomazenil, iomeglamic acid, iomeprol, iomethin, iometopane, iomorinic acid, iopamidol, iopanoic acid, iopentol, iophendylate, iophenoxic acid, iopromide, iopronic acid, iopydol, iopydone, iosarcol, isofenamic acid, ioseric acid, iosimenol, iosimide, iosulamide, iosumetic acid, iotasul, ioteric acid, iothalamate, iothalamic acid, iotranic acid, iotriside, iotrizoic acid, iotrolan, iotroxic acid, iotyrosine, iovesol, ioxabrolic acid, ioxaglic acid, ioxilan, ioxitalamic acid, ioxotrizoic acid, iozomic acid, ipamorelin, ipazilide, ipenoxazone, ipexidine, ipidacrine, ipodate, iprgratine, ipramidil, ipratropium, ipravacaine, iprazochrome, ipriflavone, iprindole, ipocinidine, iproclozide, iprocrodol, iprofenin, iproheptine, iproniazide, ipronidazole, iproplatin, iprotiazem, iproxamine, iprozilamine, ipsalazide, ipsapirone, iquindamine, iralukast, irampanel, irbesartan, irindalone, irinotecan, irloxacin, irofulven, irolapride, iroxanadine, irsogladine, irtemazole, isalidole, isalsteine, isamfazone, isamoltan, isamoxole, isatoribine, isaxonine, isbogrel, isbufylline, ispamicin, isoamilinile, isobromindione, isobucaine, isobutamben, isocarboxazid, isoconazole, isocromil, isoetharine, isoflupredone, isoflurophate, isomazole, isomerol, isometamidium, isomethadone, isometheptene, isomolpan, isoamylamine, isoniazid, isonixin, isoprazole, isoprednidene, isoprofen, isopropamide, isopropicillin, isoproterenol, isosrbide, isospaglumic acid, isosulfan blue, isosulpride, isothipendyl, isotiquimide, isotretinoin, isoxaprolol, isoxepac, isoxicam, isoxsuprine, isradipine, israpafant, istrdefylline, itameline, itanoxone, itasetron, itazigrel, itopride, itraconazole, itriglumide, itrocainide, itrocinonide, iturelix, ivbradine, ivarimod, ivermectin, ivoqualine, ixabepilone, izonsteride, josamycin, kainic acid, kalafungin, kanamycin, kebuzone, keracyanin, ketamine, ketanserin, ketazocine, ketazolam, kethoxal, ketipramine, ketobemidone, ketocaine, ketocainol, ketoconazole, ketoprofen, ketorfanol, ketorolac, ketotifen, ketotrexate, khellin, khelloside, kitasamycin, labetalol, labradimil, lachesine, lacidipine, lacosamide, lactalfate, lactilol, lactulose, ladirubicin, ladostigil, laflunimus, lafutiine, laidlomycin propionate, lamifiban, lamivudine, lamotrigine, lamitidine, lanatoside, landiolol, lanepitant, lanicemine, laniquidar, lanoconazole, lanperisone, lanproston, lanreotide, lansoprazole, lapatinib, lapisteride, laprafylline, lapyrium, laquinimod, lasalocid, lasinavir, lasofoxifene, latanoprost, laudexium, laurcetium, laurocapram, lauroguadine, laurolinium, lauryl isoquinolinium, lavoltidine, lazabemide, lecimibide, ledazerol, ledoxantrone, lefetamine, leflunomide, lefradafiban, leiopyrrole, lemidosul, lemidipine, leminoprazole, lemoxinol, lemuteporfin, lanalidomine, lenampicillin, lenapenem, leniquisin, leuperone, leptacline, lercanidipine, lergotrile, lerisetron, lesoptiron, lestaurtinib, leteprinim, leteprinim, letimide, letosteine, letrazuril, letrozole, leucinocaine, leucocianidol, leucovorin, leurubicin, levalbuterol, levallorphan, levamfetamine, levamisole, levcromakalim, levcycloserine, levdobutamine, levemoamil, levetiracetam, levisoprenaline, levlofexidine, levmetamfetamine, levobetaxolol, levobunolol, levobupiacaine, levocabastine, levocamitine, levodopa, levodropropizine, levofacetoperane, levofenfluramine, levofloxacin, levofluraltadone, levoleucovorin, levomenol, levomepromazine, levomethadone, levomethadyl acetate, levomethorphan, levometiomeprazine, levomoprolol, levomoramide, levonantradol, levonordefrin, levonorgestrel, levophenacylmorphan, levopropoxyphene, levopropylcilline, levopropuylhexedrine, levoprotiline, levorin, levormeloxifene, levorphanol, levosalbutamol, levosemotiadil, levosimendan, levosulpiride, levothyroxine, levotofisopam, levoxadrol, lexipafant, lexithromycin, lexofenac, liarozole, libecillide, libenzapril, licarbazepine, licofelone, licostinel, lidadronic acid, lidamine, lidanserin, lidocaine, lidoferin, lidorestat, lifariaine, lifibrate, lifibrol, lilopristone, limaprost, limazocic acid, linarotene, lincomycin, lindane, linetastine, linezolid, linogliride, linopirdine, linotroban, lisinidomine, lintitript, lintopride, liothyronine, lipoic acid, liraglutide, liranaftate, lirequinil, lirexapride, lirimilast, liroldine, lisadimate, lisinopril, lisofylline, lisuride, litomeglovir, litoxetine, litracen, lividomycin, lixazinone, lixivaptan, lobapolatin, lobeline, lobendazole, lobenzarit, lobucavir, lobuprofen, locicortolone, lodaxaprine, lodazecar, lodelaben, lodenosine, lodinixil, lodiperone, lodoxamide, lofemizole, lofendazam, lofentanil, lofepramine, lofexidine, loflucarban, lombazole, lomefloxacin, lomeguarib, lomerizine, lometraline, lometrexol, lomevactone, lomifylline, lomofungin, lomustine, lonafarnib, lonapalene, lonaprofen, lonazolac, lonidamine, loperamide, lopinavir, lopirazepam, lopobutan, loprazolam, loracarbef, lorajmine, lorapride, lorazepam, lorbamate, lorcainide, lorcinadol, loreclezole, lorglumide, lormetazepam, lornoxicam, lopiprazole, lortalamine, lorzafone, losartan, losigamone, losindole, losmiprofen, losoxantrone, losulazine, loteprednol, lotrafiban, lotrifen, lotucaine, lovastatin, loviride, loxanast, loxapine, loxiglumide, loxoprofen, loxoribine, lozilurea, lubazodone, lubeluzole, lubiprostone, lucanthone, lucartamide, lucimycin, lufenuron, lufironil, lufuradom, luliconazole, lumiracoxib, lupitidine, luprostiol, lurasidone, lurosetron, lurototecan, lusaperidone, luxabendazole, lydimycin, lymecycline, lynestrenol, lypressin, mabuprofen, mabuterol, maduramicin, mafenide, mafoprazine, mafosfamide, malathion, maleylsulfathiazole, malotilate, mangafodipir, manidipine, manifaxine, mannomustine, manozodil, mantabegron, mapinastine, maprotiline, maraviroc, marbofloxacin, maribavir, maridomycin, marimastat, mariptiline, maropitant, maroxepin, masoprocol, maxacalcitol, maytansine, mazapertine, mazaticol, mazindol, mazipredone, mazokalim, mebanazine, mebendazole, menbenoside, mebeverine, mebezonium, mebhydrolin, mebiquine, mebolazine, mebrofenin, mebutamate, mebutizide, mecamylamine, mecarbinate, mecetronium, meciadanil, mecinarone, meclinertant, meclizine, meclocycline, meclofenamaic acid, meclofenoxate, meclonazepam, mecloqualone, meclorisone dibutyrate, mecloxamine, mecobalamin, medazepam, medazomide, medetomidine, medibazine, medifoxamine, medorinone, medorubicin, medrogestrone, medronic acid, medroxalol, medroxyprogesterone acetate, medrylamine, medrysone, mefeclorazine, mefenamic acid, mefenidil, mefenidramium, mefenorex, mefeserpine, mefexamide, mefloquine, mefruside, megalomyciin, megestrol, megace, meglitinide, meglucycline, meglumine, meglutol, meladrizine, melagatran, melarsomine, melarsonyl, melarsoprol, meldonium, melengestrol acetate, meletimide, melevodopa, melinamide, melitracen, melizame, meloxicam, melperone, melphalan, melquinast, meluadrine, mamantine, memotine, menabitan, menadiol, menadione, menadoxime, menatetrenone, menbutone, menfegol, menglytate, menitrazepam, menoctone, menogaril, menobentine, mepazine, mepenzolate, meperidine, mephenesin, mephenoxalone, mephentermine, mephenyloin, mephobarbital, mebaral, mepindolol, mepiperphenidol, mepiprazole, mepiroxol, mepitiostane, mepivacaine, mepixanox, mepramidil, meprednisone, meprobamate, meprochol, meproscillarin, meprotixol, meprylcaine, meptazinol, mequidox, mequinol, mequitamium, mequitazine, meradimqate, menthyl anthranilate, merafloxacin, meralein, meralluride, merbaphen, merbromin, mercaptomerin, mercaptopurine, mercuderamide, mercufenol, mercumatilin, mergocriptine, meribendan, merimepodib, meropenem, mersalyl, mertialide, mesabolone, mesalamine, meseclazone, mesocarb, mesoridazine, mesipiperone, mespirenone, mestanolone, mesterolone, mestranol, mesudipine, mesulergine, mesulfamide, mesulfen, mesuprine, metabromsalan, metbutethamine, metabutoxycaine, metacetamol, metaclazepam, metacresol, metaglycodol, metahexamide, metalkonium, metalol, metamelfalan, metamfazone, metamfenpramone, metampicillin, metanixin, metapramine, metaproterenol, metaraminol, metaxalone, metazamide, metazide, matazocine, metbufen, meteneprost, metergoline, metergotamine, metescufylline, metesculetol, metesind, metethoheptazine, metformin, methacholine, methacycline, methadone, methadyl acetate, methallenestril, methallibure, methalthiazide, methamphetamine, methandriol, methandrostenolone, methaniazide, methantheline, methaphenilene, methapyrilene, methaqualone, metharbital, methastyridone, methazolamide, methdilazine, methenamine, methenolone, mepheptazine, methestrol, methetoin, methikcillin, methimazole, methiodal, methiomeprazine, methionine, methisazone, methitural, methixene, methocarbamol, methocidin, methohexital, methopholone, methoprene, methoserpidine, methotrexate, methotrimeprazine, methoxamine, methoxsalen, methoxyphedrine, methoxyphenamine, methoxypromazine, methscopolamine, methsuximide, methyclothiazide, methyl aminolevulinate, methyl palmoxirate, methyl salicylate, methylatropine, methylbenactyzium, methylbenzethonium, methylcromone, methyldesorphine, methyldihydromorphine, methyldopa, methylene blie, methylephedrine, methylergometrine, methylergonovine, methylparaben, methylphenidate, methylprednisolone, methyltestosterone, methylthiouracil, methynodiol, methyprylon, methysergide, metiamide, metiapine, metiazinic acid, metibride, metricrane, metildigoxin, metindizate, metioprim, metioxate, metipirox, metiprenaline, metitepine, metizoline, metkephamid, metochalcone, metocinium, metoclopramide, metocurine, metofenazate, metogest, metolazone, metomidate, metopimazine, metopon, metoprine, metoprolol, metoquizine, metoserpate, metostilenol, metoxepin, metrafazoline, metralindole, metrazifone, metrenperone, metribolone, metrifonate, metrifudil, metrizamide, metrizoate, metronidiazole, meturedepa, metyrapone, metyrosine, mevastatin, mexafylline, mexazolam, mexenone, mexiletine, mexiprosil, mexoprofen, mexrenoate, mezacopride, mezepine, mezilamine, mezlocillin, miaanserin, mibefradil, mibolerone, miboplatin, micafungin, miconazole, micronomicin, midaflur, midafotel, midaglizole, midamaline, midaxifylline, midazogrel, midazolam, midecamycin, midestein, midodrine, midostaurin, mifentidine, mifepristone, mifobate, miglitol, miglustat, mikamycin, milacainide, milacemide, milameline, milataxel, milenperone, milfasartan, milipertine, miloxacin, milrinone, miltefosine, milverine, mimbane, minalrestat, minamestane, minaprine, minaxolone, mindodilol, mindoperone, minepentate, minocromil, minocycline, minodronic acid, minopafant, minoxidil, mioflaazine, mipitroban, mipragoside, miproxifene, mirfentanil, mirincamycin, miripirium, miriplatin, mirisetron, miristalkonium, miroprofen, mirosamicin, mirostipen, mirtazapine, misonidazole, misoprostol, mitemcinal, mitiglinide, mitindomine, mitobronitol, mitocarcin, mitoclomine, mitocromin, mitoflaxone, mitogillin, mitoguazone, mitolactol, mitomalcin, mitomycin, mitonafide, mitopodozide, mitoquidone, mitosper, mitolane, mitotenamine, mitoxantrone, mitozolomide, mitradipide, mivacurium, mivobulin, mivotilate, mixidine, mizolastine, mizoribine, mobecarb, mobenzoxamine, mocimycin, mociprazine, moclonemide, moctamide, modafinil, modaline, modecainide, modipafant, moexipril, moexiprilat, mofarotene, mofebtazone, mofegiline, mofezolac, mofloverine, mofoxine, mofuisteine, molfarnate, molinazone, molindone, molracetam, molsidomine, mometasone, monalazone, monatepil, monesin, monobenzone, monoctanoin, monometacrine, monophosphothiamine, monoxerutin, montelukast, monterelin, moperone, mopidamol, mopidralazine, moprolol, moquizone, morantel, morazone, morclofone, morforex, moricizine, morinamide, momiflumate, morocromen, moroxydine, morpheridine, morphine, morsuximide, mosapramine, mosapride, motapizone, motexafin, motrazepam, motrtinide, moveltipril, moxadolen, moxalactam, moxaprindine, moxastine, moxaverine, moxazocine, moxestrol, moxicoumone, moxidectin, moxifloxacin, moxilubant, moxipraquine, moxirapine, moxisylate, moxnidazole, moxonidine, mozavaptan, mozenavir, mubritnib, mupirocin, murabutide, muraglitazar, mureletecan, murocainide, muzolimine, mycophenolic acid, myfadol, myrophine, myrtecaine, nabazenil, nabilone, nabitan, naboctate, nabumetone, nacartocin, nadide, nadiofloxacin, nadolol, nadoxolol, nafagrel, nafamostat, nafarelin, nafazatrom, nafcaproic acid, nafcillin, nafenodone, nafenopin, nafetolol, nafimidone, nafiverine, naflocort, nafomine, nafoxadol, nafoxidine, nafronyl, naftalofos, naftazone, naftifine, naftopidil, naftoxate, naftypamide, naglivan, nalbuphine, nalfurafine, nalidixic acid, nalmefene, nalmexone, nalorphine, naloxone, naltrexone, naminidil, naminterol, namirotene, namoxyrate, nanafrocin, nandrolone, nanterinone, nantradol, napactadine, napamezole, naphazaoline, naphthonone, napirimus, napitane, naproxime, naproxen, naproxol, napsagatran, naranol, narasin, naratriptan, nardetoterol, naroparcil, natamycin, nateglinide, navuridine, naxagolide, naxaprosteine, naxifylline, nealbarbital, nebantan, nebidrazine, nebivolol, neboglamine, nebracetam, nebramycin, necopidem, nedaplatin, nedocromil, nefazodone, nefiracetam, neflumozide, nefopam, nelarabine, neldazosin, nelezaprine, nelfinavir, neltenexine, nelzarabine, nemadectin, nemazoline, nemifitide, nemonapride, nemorubicin, neocinchophen, neomycin, neostigmine, nepadutant, nepafenac, nepaprazole, nepicastat, nepinalone, nequinate, neramexane, neraminol, nerbacadol, neridronic acid, nerisopam, nesapidil, nesiritide, nesosteine, nestifylline, neticonazole, netilmicin, netivudine, netobimin, netoglitazone, netupitant, neutramycin, neviparine, nexeridine, nexopamil, niacin, niacinamide, nialamide, niaprazine, nibroxane, nicafenine, nicainoprol, nicametane, nicanartine, nicaraven, nicarbazin, nicardipine, nicergoline, niceritol, niceverine, niclofolan, niclosamide, nicoboxil, nicoclonate, nicocodine, nicocortonide, nicocidodine, nicoduozide, nicofibrate, nicofuranose, nifurate, nicogrelate, nicomol, nicomorphine, nicopholine, nicoracetam, nicorandil, nicothiazone, nicotredole, nicoxamat, nictiazem, nictindole, nidroxyzone, nifedipine, nifekalant, nifenalol, nifenazone, niflumic acid, nifungin, nifiradene, nifuraldezone, nifuralide, nifuratel, nifuratrone, nifurdazil, nifurethazone, nifurfoline, nifurimide, nifurizone, nifurmazole, nifurmerone, nifuroquine, nifuroxazide, nifuroxime, nifurpipone, nifurpirinol, nifirprazine, nifurquinazol, nifursemizone, nifursol, nifurthiazole, nifurtimox, nifurtoinol, nifurvidine, nifurzide, nigludipine, nihydrazone, nikethamide, nileprost, nilprazole, niludipine, nilutamide, nilvadipine, nimazone, nimesulide, nimetazepam, nimidane, nimodipine, nimorazole, nimustane, neometacin, niperotidine, nipradilol, niprofazone, nitavoline, nirdazole, nisbuterol, nisobamate, nisoldipine, nisoxetine, nisterime, nitarsone, nitazoxanide, nitecapone, nithiamide, nitisinone, nitracrine, nitrafudan, nitralamine, nitramisole, nitraquazone, nitrazepam, nitrefazole, nitrendipine, nitrocefin, nitroclofene, nitrocycline, nitrodan, nitrofurantoin, nitrofurazone, nitromersol, nitromide, nitromifene, nitroscanate, nitrovin, nitroxinil, nitroxoline, nivazol, nivimedone, nizatidine, nizofenone, noberastine, nocloprost, nocodazole, nofecainide, nogalamycin, nolatrexed, nolinium, nolomirole, nolpitantium, nomegestrol, nomelidine, nomifensine, nonabine, nonaperone, nonapyrimine, nonathymulin, nonivamide, noracymethadol, norbolethone, norbudroine, norcholestenol, norclostebol, norcodeine, nordazepam, nordefrin, nordinone, norelgestromin, norepinepherine, norethandrolone, noethindrone, norethynodrel, noreximide, norfenefrine, norfloxacin, norgesterone, norgestimate, norgestomet, norgestrel, norgestrieneone, norletimol, norlevorphenol, normethadone, normorphine, norpipanone, nortetrazepam, nortopixantrone, nortriptyline, norvinisterone, nosantine, noscapine, nosiheptide, novobiocin, noxiptiline, noxytiolin, nuclomedone, nuclotixene, nufenoxole, nupafant, nuvenzepine, nylestriol, nylidrin, nystatin, obidoxime, ocaperidone, ocfentanil, ociltide, ocinaplon, octacaine, octafonium, octamoxin, octapinol, octatine, octaverine, octazamide, octenidine, octicizer, octimibate, octinoxate, octisalate, octocrylene, octodrine, octopamine, octotiamine, octreotide, octriptyline, octriazole, odalprofen, odapipam, odiparcil, ofloxacin, ofomine, oftasceine, oglufanide, olaflur, olamufloxacin, olanexidine, olanzapine, olaquindox, olcegepant, oleandomycin, oletimol, olmesartan, olopatadine, olpadronic acid, olpimedone, olprinone, olradipine, olsalazine, oltipraz, olvanil, omaciclovir, omapartrilat, omeprazole, omidoline, omigapil, omiloxetine, omoconazole, omonasteine, onapristone, ondansetron, ontazolast, ontianil, opanixil, opaviraline, opiniazide, opipramol, opratonium, orazamide, orazipone, orbofiban, orbutopril, orconazole, orientiparcin, oritavancin, orlistat, ormaplatin, ormeloxifene, ormetoprin, ornidazole, ornipreessin, ornithine, ornoprostil, orotic acid, orotirelin, orpanoxin, orphenadrine, ortataxel, orteteamine, osanetant, osaterone, oseltamivir, osemozotan, osmadizone, ospemifene, ostreogrycin, osutidine, otamixaban, otenzepad, oteracil, otilonium, otimerate, ouabain, oxabolon, oxabrexine, oxaceprol, oxacillin, oxadimedine, oxaflozane, oxaflumazine, oxagrelate, oxalinast, oxaliplatin, oxamarin, oxametacin, oxamisole, oxaminiquinem oxanamide, oxandrolone, oxantel, oxapadol, oxapium, oxaprazine, oxaprotiline, oxaprozin, oxcarbazole, oxatomide, oxazafone, oxazepam, oxazidone, oxazolam, oxazorone, oxcarbazepine, oxdralazine, oxeclosporin, oxedrine, oxeglitazar, oxeladin, oxendolone, oxepinac, oxetacillin, oxethazine, oxetorone, oxfendazole, oxfenicine, oxibendazole, oxibetaine, oxiconizole, oxidapamine, oxidronic acid, oxfentorex, oxifungin, oxigluttione, oxilofrine, oxilorphan, oximonam, oxindanac, oxiniacic acid, operomide, oxiracetam, oxiramide, oxisopred, oxisuran, oxitefonium, oxitriptan, oxitriptyline, oxtriponium, oxmetidine, oxodipine, oxogestone, oxolamine, oxolinic acid, oxomermazine, oxonazine, oxophenarsine, oxoprosto;l, oxpheneridine, oxprenoate, oxprenolol, oxtriphylline, oxbenzone, oxybutynin, oxychlorosene, oxycinchophen, oxyclipine, oxyclozanide, oxycodone, oxydipentonium, oxyfedrine, oxymesterone, oxymetazoline, oxymethalone, oxymorphone, oxypendyl, oxypertine, oxyphenbutazone, oxyphencyclimine, oxyphenisatin, oxyphenonium, oxypurinol, oxypurronium, oxyquinoline, oxyridazine, oxysonium, oxytetracycline, oxytocin, ozagrel, ozagamicin, ozolindone, paclitaxel, pacrindolol, pactimibe, padimate A, padimate Q, pafenolol, pagoclone, paldimycin, palinavir, paliperidone, palmidrol, palmoxirate, palonidipine, palonosertron, palosuran, pamabron, pamaqueside, pamaquin, pamicogrel, pamidronic acid, panadiplon, panamesine, pancopride, pancuronium, panipenem, panomifene, pantenicate, pantethine, panthenol, pantoprazole, panuramine, papverine, papveroline, parachlorphenol, paraflutizide, paramethadione, paramethasone acetate, paranitrosulfathiazole, paranyline, parapenzolate, parapropamol, pararosaniline, paraxazone, parbendazole, parcetasal, parconazole, parecoxib, pareptide, parethoxycaine, pargeverine, pargolol, pargyline, paricalcitol, paridocaine, parodilol, paromomycin, paroxetine, paroxypropione, parsalmide, particin, parvaquone, pasiniazid, pasireotide, patamostat, patupilone, paulomycin, paxamate, pazelliptine, pazinaclone, pazoxide, pazufloxacin, pecilocin, pecocycline, pefloxocin, pelanserin, peldesine, peliomycin, pelitinib, pelitrexol, pelretin, pelrinone, pelubiprofen, pemedolac, pemerid, pemetrexed, pemirolast, pemoline, penamecillin, penbutolol, penciclovir, pendecamine, pendetide, penfluridol, penflutizide, pengitoxin, penicillamine, penicillin G, penicillin V, penimepicycline, penimocycline, penirolol, penmesterol, penoctonium, penprostene, pentabamate, pentacynium, pentfluranol, pentagastrin, pentagestrone, pentalamide, pentamethonium, pentamidine, pentamorphone, pentamoxane, pentamustine, pentapiperide, pentapiperium, pentaquine, pentazocine, pentetic acid, pentreotide, penthienate, penthrichloral, pentiapine, pentifylline, pentigetide, pentisomicin, pentisomeide, pentizidone, pentobarbital, pentolinium, pentolonium, pentomone, pentopril, pentorex, pentosalen, pentostatin, pentoxifylline, pentoxyverine, pentrinitrol, pentylenetetrazol, peplomycin, pepstatin, peraclopone, peradoxime, perafensine, peralopride, peramivir, peraquisin, perastine, peratizole, perazine, perbufylline, perfomedil, perfosfamide, pegolide, perhexiline, periciazine, perifosine, perimetazine, perindopril, perindoprilat, perisoxal, perlapine, permethrin, perospirone, perphenazine, persilic acid, perzinfotel, petrichloral, pexantel, phanquone, phenacaine, phenacemide, phenacetin, phenactropinium, phenadoxone, phenaglycodol, phenamazoline, phenampromide, phenaphthazine, phenarsone, phenazocine, phenazopyridine, phenbutazone, phencarbamide, phencyclidine, phendimetrazine, phenelzine, pheneridine, phenethicillin, pheneturide, phenylglutarimide, phenicarbazide, phenindamine, phenindione, pheniprazine, pheniramine, phenisonone, phenmetrazine, phenobarbital, phenobutiodil, phenomorphan, phenothiazine, phenothrin, phenoxybenzamine, phenoxypropazine, phenprobamate, phenprocoumon, phenpromethamine, phensuximide, phentermine, phentolamine, phenyl aminosalicylic acid, phenylalanine, phenylbutazone, phenylephrine, phenylpropanolamine, phenylthiolone, phenyltoloxamine, phenyracillin, phenyramidol, phenyloin, pnetharbital, pholcodine, pholedrine, phoxim, phthalofyne, phthylsulfacetamide, phthalylsulfamethiazole, phthalylsulfathiazole, physostigmine. Phytic acid, phytonadione, pibaxizine, pibecarb, piberaline, piboserod, pibrozelesin, pibutidien, picafibrate, picartamide, picenadol, picilorex, piclamilast, piclonidine, piclopastine, picloxydine, picobenzide, picodralazine, picolamine, piconol, picoperine, picoplatin, picoprazole, picotamide, picotrin, picumast, picumeterol, pidobenzone, pidolacetamol, pidolicaicd, pidotimod, pifarnine, pifinate, pifexole, piflutixol, piketoprofen, pildralazine, pilocarpine, pilsicainide, pimagedine, pimeclone, pimecrolimus, pimefylline, pimelautide, pimetacin, pimethixene, pimetine, imetremide, pimilprost, piminodine, pimobendan, pimonidazole, pimozide, pinacidil, pinadoline, pinafide, pinaverium, pinazepam, pincainide, pindolol, pinokalant, pinolcaine, pinoxepine, pioglitazone, pipacycline, pipamazine, pipamperone, pipazethate, pipebuzone, pipecuronium, pipemidicacid, pipendoxifene, pipenzolate, pipequaline, piperacetazine, piperacillin, piperamide, piperidolate, piperilate, piperocaine, piperonyl butoxide, piperoxan, piperphenidol, piperylone, pipobroman, pipoctanone, pipofezine, piposulfan, pipotiazine, pipoxizine, pipoxolan, pipradimadol, pipradrol, pipramadol, pipratecol, piprinhydrinate, pipocurarium, piprofurol, piprozolin, piquindone, piquizil, piracetam, pirandamine, pirarubicin, piraxelate, pirzmonam, pirazolac, pirbenicillin, pirbuterol, pirdonium, pirenoxine, pirenperone, pirezepine, pirepolol, piretanide, pirfenidone, pirbendil, piridicillin, piridocaine, piridoxilate, piridronic acid, pirifibrate, pirimiphos-ethyl, pirindazole, pirinixic acid, pirinixil, piriprost, piriqualone, pirisudanol, piritramide, piritrexin, pirlimycin, pirlindole, pirmagrel, pirmenol, pirnabine, piroctone, pirodavir, priodomast, pirogliride, piroheptine, pirolate, pirolazamide, piromidic acid, piroxantrone, piroxicam, piroxicillin, piroximone, pirozadil, pirprofen, pirquinozol, pirralkonium, pirsidomine, pirtenidine, pitenodil, pitofenone, pituxate, pivagabine, pivampicillin, pivenfrine, pivopril, pivoxazepam, pixantrone, pizotyline, plafbride, plaunotol, plauracin, pleconaril, pleuromulin, plevitrexed, plicamuycin, plomestane, pobilukast, podilfen, podofilox, poldine, polymixin, polythiazide, pomisartan, ponalrestat, ponazuril, ponfibrate, porfiromycin, posaconazole, posatirelin, posizolid, poskine, practolol, pradolfoxacin, prajmalium, pralatrexate, pralidoxime, pralmorelin, pralnacasan, pramipexole, pramiracetam, pramoxine, prampine, pranazepide, pranidipine, prankulast, pranolium, pranoprofen, pranosal, prasterone, prasugrel, pratosartan, pravadoline, pravastatin, praxadine, prazarelix, prazepam, prazepine, praziquantel, prazitone, prazocillin, prazosin, preclamol, prednazate, prednazoline, prednicarbate, prednimustine, prednisolamate, prednisolone, prednisone, prednival, prednylidene, pregabalin, pregnadiol, pregnenolone, premafloxacin, premazepam, prenalterol, prenisteine, prenoverine, prenoxdiazine, prenylamine, pretamazium, pretiadoil, prezatide, pribecaine, pridefine, prideperone, pridinol, prifelone, prifinium, prifuroline, pilocalne, primaperone, primaquine, primidolol, primidone, primycin, prinomastat, prinomide, prinoxodan, pristinol, pristinamycin, prizidilol, proadifen, probarbital, probenecid, probicromil, probucol, procainamide, procaine, procarbazine, procaterol, prochlorperazine, procinolol, procinonide, proclonol, procromil, procyclidine, procymate, prodeconium, prodilidine, prodipine, prodolic acid, profadol, profexalone, proflavine, proflazepam, progabide, progesterone, proglumetacin, proglumide, proheptazine, proligestone, praline, prolintane, prolonium, promazine, promegestone, promestriene, promethazine, promolate, promoxolane, prontalol, propacetamol, propafenone, propagermanium, propamidine, propanidid, propanocaine, propantheline, proparacaine, propatyl nitrate, propazolamide, propenidazole, proprntofylline, propenzolate, properidine, propetamide, propetamfos, propetandrol, propicillin, propikacin, propinetidine, propiomazine, propiocaine, propiram, propisergide, propiverine, propizepine, propofol, propoxate, propoxur, propoxycaine, propoxyphene, propranolol, propyl docetrizoate, propyl gallate, propylhexedrine, propyliodone, propylthiouracil, propyperone, propyphenazone, propyromazine, proquazone, proquinolate, prorenoate, proroxan, prscillardin, prospidium, prostalene, prosulpride, prosultiamine, proterguride, protheobromine, prothipendyl, prothixene, protiofate, protionamide, protirelin, protizinic acid, protokylol, protoporphyrin, protriptyline, proxzole, proxibarbal, proxibutene, proxicromil, proxifezone, proxorphan, proxymetacaine, proxyphylline, prozapine, prucalopride, prulifloxacin, pruvanserin, pseudoephedrine, pumafentrine, pumaprazole, pumitepa, pumosetrag, puromycin, pyrabrom, pyrantel, pyrathiazine, pyrazinamide, pyrazofurin, pyricarbate, pyridarone, pyridinol, pyridofylline, pyridostigmine, pyridoxal, pyridoxamine, pyridoxine, pyrilamine, pyrimethamine, pyrimate, pyrinoline, pyrithione, pyrithyldione, pyritidium, pyritinol, pyrophenindane, pyrovalerone, pyroxamine, pyrrobutamine, pyrrocaine, pyrrolifene, pyrroliphene, pyrrolnitrin, pyrroxane, pyrvinium, pytamine, quadazocine, quadrosilan, quatacaine, quazepam, quazinone, quazodine, quazolast, quetiapine, quifenadine, quiflapon, quillifoline, quilostigmine, quinacainol, quinacillin, quinacrine, quinagolide, quinaldine blue, quinapril, quinaprilat, quinazosin, quibolone, quincarbate, quindecamine, quindonium, quindoxin, quinelorane, quinestradol, quinestrol, quinethazone, quinetolate, quinezamide, quinfamide, quingestanol acetate, quingestrone, quinidine, quinine, quinotolast, quinpirole, quinterenol, quitiofos, quinuclium, quinupramine, quinupristin, quipazine, quisultazine, rabeprazole, raclopride, ractopamine, radafaxine, rafoxanide, ragaglitazar, ralitoline, raloxifene, raltitrexed, raluridine, ramatroban, ramciclane, ramelteon, ramifenazone, ramipril, ramiprilat, ramixotidine, ramnodigin, ramnoplanin, ramorelix, ramosetron, ranelic acid, ranimustine, ranimycin, ranirestat, ranitidine, ranolazine, rapacuronium, rasagiline, rasburicase, rathyronine, ravuconazole, razaxaban, razinodil, razobazam, razoxane, rebimastat, reboxetine, recainam, reclazepam, regadenoson, reglitazar, relcovaptan, relomycin, remacemide, remifentanil, remikiren, remiprostol, remoxipride, renanolone, rentiapril, renzapride, repaglinide, reparixin, repinotan, repirinast, repromicin, reproterol, rescimetol, rescinnamine, resequinil, reserpine, resiquimod, resocortol butyrate, resorantel, resorcinol, retapamulin, retelliptine, retigabine, retinol, revaprazan, revatropate, revenast, reviparin, revizinone, revospirone, ribavirin, riboflavin, riboprine, ribostamuycin, ricasetron, ridazolol, ridogrel, rifabutin, rifalazil, rifametane, rifamexil, rifamide, rifampin, rifapentine, rifaximin, rilapine, rilmakalim, rilmazafone, rilmenidine, rilopirox, rilozarone, rilpovorine, riluzole, rimantadine, rimazolium, rimcazole, rimexolone, rimiterol, rimonabant, rimoprogin, riodipine, rioprostil, ripazepam, ripisartan, risarestat, risedronicacid, risocaine, risotilide, rispenzepine, risperidone, ristianol, ristocetin, ritanserin, ritometan, ritipenem, ritobegron, ritodrine, ritolukast, ritonavir, ritropirronium, ritrosulfan, rivaroxaban, rivastigmine, rivoglitazone, rizatriptan, robalzotan, robenidine, rocastine, rocepafant, rociclovir, rocuronium, rodocaine, rodorubicin, rofecoxib, rofelodine, rofleponide, roflumilast, rogletimide, rokitamycin, rolafagrel, roletamide, rolgamidine, rolicyclidine, rolicyprine, rolipram, rolitetracycline, rolodine, rolziracetam, romazarit, romergoline, romifenone, romifidine, romurtide, ronactolol, ronidazole, ronifibrate, ronipamil, runnel, ropinirole, ropitoin, ropivacaine, ropizine, roquinimex, rosaprostol, rosaramicin, rose bengal, rosiglitazone, rosoxacin, rostafuroxin, rostaporfin, rosterolone, rosuvastatin, rotamicillin, rotigotine, rotoxamine, rotaxate, roxadimate, roxarsone, roxatidine acetate, roxibolone, roxifiban, roxindole, roxithromycin, roxolonium, roxoperone, rubitecan, ruboxistaurin, rufinamide, rufloxacin, rupatadine, rupintrivir, rutamycin, ruvazone, ruzadolane, sabarubicin, sabcomeline, sabeluzole, sabiporide, saccharin, safingol, safirinol, sagandipine, salacetamide, salafibrate, salantel, salazodine, salazosulfadimidine, salazosulfamide, salazosulfathiazole, salcaprozoic acid, salcolex, salethamide, salflucerine, salicyl alcohol, salicylamide, salicylic acid, salinazid, salinomycin, salmefamol, salmeterol, salmisteine, salnacedin, salprotoside, salsalate, sameridine, samixogrel, sampatrilat, sampirtine, sancycline, sanfetrinem, sanguinarium, saperconazole, saprisartan, sapropterin, saquinavir, sarafloxacin, sarakalim, saralasin, sarcolysin, sardomozide, saredutant, saripedem, sarizotan, sarmazenil, samoxicillin, sarpicillin, sarpogrelate, saterinone, satigrel, satranidazole, satraplatin, saviprazole, savoxepin, scopafungin, scopinast, scopolamine, secalciferol, seclazone, secnidazole, secobarbital, securinine, sedecamycin, sedoxantrone, seganserin, segesterone, seglitide, selamectin, selgiline, selfotel, soldenoson, selprazine, sampimod, sematilide, semaxanib, semduramicin, semorphone, semotiadil, semustine, senazodan, seocalcitol, sepazonium, seperidol, sepimostat, seprilose, seproxetine, sequifenadine, seratrodast, serazapine, serfibrate, sergolexole, sermetacin, sertindole, sertraline, setastine, setzindol, setipafant, setiptiline, setoperone, sevitropium, sevopramide, sezalamide, sagoside, sibenadet. Sibopirdine, sibrafiban, sibutramine, siccanin, sifrprazine, siguazodan, silandrone, sildenafil, silibinin, silcristin, sildianin, silodosin, silodrate, silperisone, siltenzepine, simendan, simetride, simfibrate, simtrazene, simvastatin, sincalide, sinefungin, sinitrodil, sintropium, sipatrigine, siramesine, siratiazem, sirolimus, sisomicin, sitafloxacin, sitalidone, sitamaquine, sitaxentan, sitofibrate, sitoglusoide, sivelestat, soblidotin, sobuzoxane, solabegron, solifenasin, solimastat, solpecainol, solypertine, somatadine, soneclosan, sonepiprazole, sopitazine, sopromidine, soquinolol, sorafenib, soraprazan, sorbinicate, sorbinil, sorivudine, sornidipine, sotalol, soterenol, spaglumic acid, sparfloxacin, sparfosate, sparsomycin, sparteine, spectinomycin, spiclamine, spiperone, spiradoline, spiramide, spiramycin, spirapril, spiraprilat, spirendolol, spirgetine, spirilene, spiriprostil, spirofylline, spirogermanium, spiroglumide, spiromustine, spironolactone, spiroplatin, spirorenone, spirotriazine, spiroxasone, spiroxatrine, spiroxepin, spizofurone, sprodiamine, squalamine, squalane, stacofylline, stllimycin, stannsoprfin, stanolone, stanoaolol, stavudine, stearylsufamide, steffimycin, stenbolone, strpronin, stercuronium, stevaladil, stibamine, stibophen, stilbamidine, stilbazium, stilonium, strimazole, stiripentol, stirocainide, stirofos, streptomycin, streptonicozid, streptonigrin, streptozocin, styramine, subathiazone, subendazole, succinylcholine, succinylsulfathiazole, succisulfone, suclofenide, sucralfate, sucralose, sucrose octaacetate, sucrosufate, sudexanox, sudoxicam, sufenatil, sufotidine, sufugolix, sugammadex, sulamserod, sulazepam, sulazuril, sulbactam, sulbenicillin, sulbenox, sulbentine, sulbutiamine, sulclamine, sulconazole, sulfabenz, sulfabenzamide, sulfabromomethazine, sulfacarbamide, sulfacecole, sulfacetamide, sulfachlorpyridazine, sulfachrysoidine, sulfaclomide, sulfaclorazole, sulfaclozine, sulfacytine, sulfadiazine, sulfadimethoxine, sulfadoxine, sulfaethidole, sulfaguanidine, sulfaguanole, sulfalene, sulfaloxic acid, sulfamazone, sulfamerazine, sulfameter, sulfamethaziine, sulfamethizole, sulfamethoxazole, sulfamethoxypyridazine, sulfametmidine, sulfametrole, sulfamonomethoxine, sulfamoxole, sulfanilamide, sulfanilate, sulfaanitran, sulfaperin, sulfaphenazole, sulfaproxyline, sulfapyridine, sulfaquinoxaline, sulfarsphenamine, sulfasalazine, sulfasomizole, sulfasuccinamide, sulfasymazine, sulfathiazole, sulfathiourea, sulfatolamide, sulfatroxazole, sulfatrozole, sulfazamet, sulfinaolol, sulfinpyrazone, sulfiram, sulfisomidine, sulfisoxazole, sulfobromophthalein, sulfonterol, sulforidazine, sulfosalicylic acid, sulfoxone, sulcrinat, sulindac, sulisatin, sulisobenzone, sulmarin, sulmazole, sulmepride, sulnidazole, sulocarbilate, suloctidil, sulodexide, sulofenur, sulopenem, sulosemide, sulotroban, suloxifen, sulpiride, sulprosal, sulprostone, sultamicillin, sultiame, sultopride, sultosilic acid, sultroponium, sulukast, sulverapride, sumacetamol, sumanirole, sumarotene, sumatriptan, sumetizide, sunagrel, suncillin, sunepitron, supidimide, supalast, suproclone, suprofen, suramin, suricainide, suriclone, suritozole, suronacrine, susalimod, suxemerid, suxethonium, suxibuzone, symclosene, synetine, tabilautide, tabimorelin, tacalcitol, tacapenem, tacedinaline, taclamine, tacrine, tacrolimus, tadalafil, tafluposide, taglutamine, tagorizine, talampanel, talampicillin, talaporfin, talastine, talbutal, taleranol, talibegron, talinolol, talipexole, talisomycin, tallimustine, talmetacin, talmetoprim, talnetant, talniflumate, talopram, talsalate, toloximine, talsaclidine, talsupram, taltirelin, taltobulin, taltrimide, taludipine, talviraline, tameridone, tameticillin, tametraline, tamibarotene, tamitinol, tanolarizine, tamoxifen, tampramine, tamsulosin, tanaproget, tandamine, tandospirone, tandutinib, taniplon, tanomastat, tapentadol, taprizosin, taprostene, tarazepide, tariquindar, tasosartan, tasuldine, taurolidine, tauromustine, tauroselcholic acid, taurosteine, tazadolene, tazanolast, tazarotene, tazasubrate, tazeprofen, tazifylline, taziprinone, tazobactam, tazofelone, tazolol, tazometine, tebanicline, tebatizole, tebipenem, tebufelone, tebuquine, tecadenoson, tecalcet, tecastemizole, teclthiazide, teclozan, tedisamil, tefazoline, tefenperate, teflufazine, teflutixol, tegafur, tegaserod, teglicar, teicopanin, telavancin, telbivudine, telenzepine, telinavir, telithromycin, telmesteine, telmisartan, teloxantrone, teludipine, temafloxacin, temarotene, tematropium, temazepam, temefos, temelastine, temiverine, temocapril, temocaprilat, temocillin, temodox, temoporfin, temozolomide, temisirolimus, temurtide, tenamfetamine, tenatoprazole, tendamistat, tenidap, tenilapine, teniloxazine, tenilsetam, teniposide, tenivastatin, tenocyclidine, tenofovir, tenofovir disoproxil, tenonitrozole, tenosal, tenosiprol, tenoxicam, tenylidone, teoprantil, teoprolol, tepirindole, tepoxalin, teprenone, teprotide, terazosin, terbequinil, terbinafine, terbogrel, terbucromil, terbufirol, terbuficin, terbuprol, terbutaline, terciprazine, terconazole, terdecamycin, teerestigmine, terfeadine, terflavoxate, terfluranol, terguride, teriflunomide, terikalant, terizidone, terlakiren, terlipressin, ternidazole, terodiline, terofenamate, teroxalene, teroxirone, tertatolol, tesaglitazar, tesicam, tesimide, tesimilifene, tesofensine, testolactone, testosterone, tetomilst, tetrabarbital, tetrabenazine, tetracaine, tetracycline, tetrahydrozoline, tetramethrin, tetramisole, tetraxetan, tetrazepam, tetrazolast, tetriprofen, tetrofosmin, tetronasin, tetroquinone, tetroxoprin, tetrydamine, teverelix, texacromil, tezacitabine, tezosentan, thalidomide, thebacon, thenalidine, thenium, thenyldiamine, theobromine, theodrenaline, theofibrate, theophylline, thiabendazole, thiacetarsamide, thialbarbital, thiamazole, thiamine, thiamiprine, thiamphenicol, thamylal, thiazesim, thiazinamium, thiazolsulfone, thiethyperazine, thihexinol ethylbromide, thimerfonate, thimerosal, thiocolchicoside, thioctic acid, thiofuradene, thioguanine, thiohexamide, thioinosine, thiopental, thiophanate, thiopropazate, thioproperazine, thioridazine, thiosalan, thiostrpton, thiotepa, thiotetrabarbital, thiothixene, thiphenamil, thiphencillin, thiram, thonzonium, thonzylamine, thozalinone, threonine, thymocartin, thymoctonan, thymol, thymopentin, thymotrinan, thyromedan, thyropropic acid, thyroxin, tiacrilast, tiadenol, tiafibrate, tiagabine, tiamenidine, tiametomnium, tiamulin, tianafac, tianeptine, tiapamil, tiapirinol, tiapride, tiaprofenic acid, tiaprost, tiaramide, tiazofurin, tiazuril, tiabalosin, tibeglisene, tibenelast, tibenzate, tibezonium, tibolone, tibric acid, tibrofan, ticabesine, ticalopride, ticarbodine, ticarcillin, ticlatone, ticlopidine, ticolubant, ticrynafen, tidembersat, tidiacic acid, tiemonium, tienocarbine, tienopramine, tienoxolol, tifemoxone, tifenazoxide, tiflamizole, tiflorex, tifluadom, tiflucarbine, tiformin, tifurac, tigecycline, tigemonam, tigestol, tigloidine, tilargenine, tiletamine, tilidine, tiliquinol, tilisolol, tilmacoxib, tilmicosin, tilnoprofen, tilomisole, tilorone, tilozepine, tilsuprost, tiludonic acid, timcodar, timefurone, timegadine, timelotem, timepidium, timiperone, timirdine, timobesone acetate, timofibrate, timolol, timonacic, timoprazole, tinabinol, tinazoline, tinidazole, tinisulpride, tinofedrine, tinoridine, tiocarlide, tioclomarol, tioconazole, tioctilate, tiodazosin, tiodonium, tiomergine, tiomesterone, tioperidone, tiopinate, tiopronin, tiopropamine, tiospirone, tiotidine, tiotropium, tioxacin, tioxamast, tioxaprofen, tioxidazole, tioxolone, tipentosin, tipepidine, tipetropium, tipifarnib, tipindole, tipranavir, tipredane, tiprenolol, tiprinast, tiprodil, tiprostanide, tiportimod, tiqueside, tiquinamide, tiquizium, tiracizine, tirapazamine, tiratricol, tirilazad, tirofiban, tiropramine, tisartan, tisocalcitate, tisocromide, tisopurine, tisoquone, tivanidazole, tiviciclovir, tivirapine, tixadil, tixanox, tixocortol, tizabrin, tizanidine, tizolemide, tizoprolic acid, tobicillin, toborinone, tobramycin, tocainide, tocamphyl, tocladesine, tocofenoxate, tocofibrate, tocophersolan, todralazine, tofenacin, tofetridine, tofimilast, tofisoline, tofisppam, tolafentrine, tolamolol, tolazamide, tolboxane, tolbutamide, tolvapone, tolciclate, toldimfos, tolfamide, tolfenamic acid, tolgabide, tolimidone, tolindate, toliodium, toliprolol, tolmesoxide, tometin, tolnaftate, tolnapersine, tolnidamine, toloconium, tolonidine, tolonium, toloxatone, toloxychlorinol, tolpadol, tolpentamide, tolperisone, tolpiprazole, tolpronine, tolpropamide, tolpyrramide, tolquinzole, tolrestat, tolterodine, toltrazuril, tolufazepam, tolvaptan, tolycaine, tomeglovir, tomelukast, tomoglumide, tomoxiprole, tonabersat, tonazocine, topilutamide, topiramate, topixantrone, topotecan, toprilidine, topterone, toquizine, torbafylline, torcetrapib, torcitabine, toremifene, toripristone, torsemide, tosagestin, tosifen, tosufloxacin, tosulur, trabectedin, traboxopine, tracazolate, tradecamide, tralonide, tramadol, tramazoline, trandolapril, trandolaprilat, tranexamic acid, tranilast, transcainide, trantelinium, tranycypromine, trapencaine, trapidil, travoprost, traxanox, traxoprodil, trazitiline, trazium, trazodone, trazolopride, trebenzomine, trecadrine, trecetilide, trefentanil, trelnarizine, treloxinate, trenbolone, trengestone, trenizine, treosulfan, trepibutone, trepipam, trepirium, treprostinil, treptilamine, terquisin, tresperimus, trestolone, trethinium, trethocanoic acid, tretinoin, tretinoin tocoferil, tretoquinol, triacetin, triafungin, triamcinolone, triamcinolone acetonide, triamcinolone benetonide, triamcinolone furetonide, triampyzine, triamternem triaziquone, triazolam, tribendilol, tribenoside, tribromsalan, tribuzone, tricaprilin, tricetamide, trichlorfon, trichlormethiazide, trichlomethine, triciribine, triclabendazole, triclacetamol, triclazate, triclobisonium, triclocarban, triclodazol, triclofenol, triclofos, triclofyllin, triclonide, triclosan, tricyclamol, tridihexethyl, tridolgosir, trientine, triethylenemelamine, trifenagrel, trifezolac, triflocin, triflubazam, triflumidate, triflomeprazine, trifluperazine, trifluperidol, triflupromazine, trifluidine, triflusal, trifosmin, trigevolol, trihexylpheidyl, triletide, trilostane, trimazosin, trimebutine, trimecain, trimedoxime, trimegestone, trimeperidine, trimeprazine, trimetazidine, trimethadone, trimethamide, trimethaphan, trimethidinium, trimethobenzamide, trimethoprim, trimetozine, trimetrexate, trimexiline, trimipramine, trimoprostil, trimoxamine, trioxifene, trioxsalen, tripalmitin, tripamide, triparanol, tripelennamine, triplatin, triprolidine, triptorelin, tritoqualine, trixolane, trizoxime, trocimine, troclosene, trodusquemine, trofosfamide, troglitazone, troleandomycin, tromanttadine, tropabazate, tropanserin, tropapride, tropatepine, tropenziline, tropicamide, tropigline, tropirine, tropisetron, tropodifene, troquidazole, trospectomycin, trospium, trovafloxacin, trovirdine, troxacitabine, troxerutin, troxipide, troxolamide, troxonium, troxypyrrolium, truxicurium, truxipicurium, tryparsamide, tubocurarine, tubulozole, tucaresol, tuclazepam, tulathromycin, tulobuterol, tulopafant, turosteride, tuvatidine, tybamate, tylosin, tymazolin, tyropanoate, tyrosine, tyrothricin, ubenimex, ubidecarenone, ubisindine, ufenamate, ufiprazole, uldazepam, ulifloxacin, uliprisnil, umespirone, undecylenic acid, unoprostone, upenazime, upidosin, uracil, uracil mustard, urapidil, uredepa, uredofos, urefibrate, ursodiol, urulcholic acid, utibapril, utibaprilat, vadocaine, valaciclovir, valconazole, valdecoxib, valdetamide, valdipromide, valethamate, vlaganiciclovir, valine, valnemulin, vlanoctamide, valofane, valomaciclovir, valperinol, valproate, vlaproicacid, valpromide, valrocemide, valrubicin, valsartan, valorcitabine, valtrate, vamicamide, vancomycin, vandetanib, vaneprim, vanitiolide, vanoxerine, vanyldisulfamide, vapiprost, vapreotide, vardenfanil, varenicline, varespladib, vatalanib, vatanidipine, vebufloxacin, vecuronium, vedaclidine, vedaprofen, velaresol, velnacrine, venlafaxine, venritidine, verodoline, veralipride, verapamil, verazide, verilopam, verlukast, verofylline, versetamide, verteporfin, vesnarinone, vestipitant, vetrabutine, vidarabine, vigabatrin, vilazodone, vildagliptin, viloxazine, vinbarbital, vinblastine, vinburnine, vincamine, vincanol, vincofos, vinconate, vincristine, vindeburnol, vindesine, vinpidine, vinflunine, vinformide, vinfosiltine, vinglycinate, vinleucinol, vinleurosine, vinmegallate, vinorelbine, vinpocetine, vinpoline, vinrosidine, vintiamol, vintoperol, vintriptol, vinylbital, vinzolidine, viomycin, viprostol, viqualine, viquidil, virginiamycin, viridofulvin, viroxime, visnadine, visnafylline, vofopitant, voglibose, volazocine, volpristin, voriconazole, vorozole, voxergolide, xaliproden, xamoterol, xanomeline, xanoxic acid, xanthinol, xantifibrate, xantocillin, xantofyl palmitate, xemilofiban, xenalipin, xenazoic acid, xenbucin, xenipentone, xenothiorate, xenygloxal, xenylhexenicacid, xenylropium, xibenolol, xibornol, xidecaflur, xilobam, ximelagatran, ximoprofen, xinidamine, xinomiline, sipamide, xipranolol, xorphanol, xylamidine, xylazine, xylocoumarol, xylometazoline, xyloxemine, yohimbic acid, zabicipril, zabiciprilat, zacopride, zafirlukast, zafuleptine, zalcitabine, zalderide, zaleplon, zalospirone, zalitidine, zaltoprofen, zamifenacin, zanamivir, zanapezil, zankiren, zanoterone, zapizolam, zaprinast, zardaverine, zatebradine, zatosetron, zelandopam, zenarestat, zenazocine, zeniplatin, zepastine, zeranol, zetidoline, zidapamide, zidometacin, zidovudine, zifrostilone, zilantel, zilascorb, zileuton, zilpaterol, zimeldine, zimiidoben, zindotrine, zindoxifene, zinconazole, zinostatin, zinterol, zinviroxime, zipeprol, ziprsidone, zocainone, zofenopril, zofenoprilat, zoficonazole, zolamine, zolasartan, zolazepam, zolendronic acid, zolenzepine, zolertine, zolimidine, zoliprofen, zolmitriptan, zoloperone, zolpidem, zomebazam, zomepirac, zometapine, zonampanel, zoniclezone, zoniporide, zonisamide, zopiclone, zopolrestat, zorbamycin, zorubicin, zosuquidar, zotepine, zoticasone, zoxazolamine, zucapsaicin, zuclomiphene, zuclopenthixol, and zylofuramine.

The solvent, as mentioned, can be any liquid in which the material dissolves; the solvent can be a single substance or a mixture of co-solvents, the important point being that the material to be lyophilized goes into solution. Solvents useful in the invention include materials that are liquid at room temperature, dissolve the material, and are volatilizable or sublimatable at the temperature and pressure conditions of the primary drying step discussed below. Since not all solvents dissolve all materials, some of the potential solvents will not be solvents in particular cases. Those of ordinary skill will know which liquids are suitable as solvents once the material to be lyophilized has been selected, by reference to standard texts in the field or by the conduct of simple dissolution testing of the material with the potential solvent. The chosen solvent will either alone dissolve the material or together with a co-solvent will dissolve the material in question. Co-solvents are selected from the same class as solvents, are miscible with the chosen solvent, and generally aid the dissolution of the material in the solvent. Once the material in question is selected and the solvent and any co-solvent is selected, the anti-solvent is also selected from the same set of substances, but limited to those which do not significantly dissolve the material, preferably do not dissolve the material at all, and yet are miscible with the chosen solvent/optional co-solvent system previously selected. For purposes of the present invention, solubility of the material in the solvent or solvent/cosolvent mixture is critical only in that the material needs to be dissolved. The concentration of the material in the solvent or solvent/co-solvent mixture is only of concern in certain situations. For example, in pharmaceutical injectable formulations, where the material is lyophilized in containers that, once reconstituted in the container contain unit dosage of the material for administration, materials requiring a small unit dose may utilize a significant volume of "solvent" in the lyophilization procedure. However, where the material requires a large unit dose, the liquid chosen as the solvent must necessarily be a much better solvent for the material so that the amount of solvent needed to dissolve the unit dose is amenable to being placed in the lyophilization container for processing economically. While these same concerns are important to bulk lyophilization procedures as well, they are less stringent than where the lyophilization containers are intended as the reconstitution container having unit doses. Thus, the choice of a liquid as a solvent or a co-solvent not only depends upon the intrinsic ability to dissolve the material in question, but on its relationship to the amount of the solution that can be placed in the lyophilization container intended to have a specific amount of end lyophilizate. Those of ordinary skill in the art will appreciate these concerns and be able to readily modify their particular choices to accommodate these concerns. Similar concerns apply to the choice of anti-solvent.

The lyophilization procedures herein can also be used to prepare rapidly disintegrating tablets that dissolve in the mouth without the need for water to swallow the tablet. Currently available rapidly dissolving tablets (technology owned by Zydus) is only applicable to hydrophilic molecules having a low unit dose requirement (generally less than about 15 mg per dose) which do not require taste-masking. The current invention, on the other hand, permits creating a lyophilizate in a tablet mold so that the lyophilizate takes the shape of a tablet. Since the present lyophilization method can omit virtually all auxiliary materials if the drug doesn't require taste masking, it is applicable to materials having a high unit dose amount (hundreds to more than 1 gram per unit dose), as well as to those having small unit dosage amounts. Furthermore, while the Zydus technology is available only with respect to hydrophilic materials, the present invention is applicable to both hydrophilic and hydrophobic materials.

Suitable, non-limiting, liquids for use as solvents, co-solvents, or anti-solvents, depending on the circumstances as outlined elsewhere in this specification include, but are not limited to water, 5-7 membered heteroring systems (the heteroring systems having 1-3 heteroatoms, where the heteroatoms are oxygen or sulfur, the sulfur atoms being unsubstituted or further carrying one or two oxygen substituents, except that two oxygen atoms cannot be in adjacent ring positions, for example tetrahydrofuran (THF), tetrahydropyran, dioxane, trioxane and other cyclic mono-, di- and tri-ethers), lower alkanols (such as ethanol, propanol, isopropanol, sec-butanol, t-butyl alcohol, and n-butyl alcohol), or other organic solvents that freeze in the range of a lower temperature of about −100° C., preferably −90° C., more preferably −80° C., and an upper temperature of not more than about 25° C., preferably not more than about 20° C., even more preferably not more than about 15° C., still more preferably not more than about 10° C., In addition, PEG 600-6000 and tocopherol succinate and acetate can also be used.

Preferably, the solvent is water, especially for hydrophilic materials. Water is preferred in the context of pharmaceuticals, veterinary products, and foodstuffs because any residual solvent that remains with the solid is innocuous once the lyophilizate is reconstituted with water. In applications in industries other than the above or where the freeze dried product is desired as a reactant in further reactions, other solvents, both within and beyond those set forth above may be preferred as well and will be well within the ordinary skill of those in the art. Nonetheless, the solvent must be one that is volatile or sublimates under the primary drying step conditions. Other preferable liquids for use in the invention as the solvent or as the co-solvent or as the anti-solvent as dictated by the particulars of the material in question include ethanol, tetrahydrofuran, and dioxane.

If desired, a co-solvent may be used to aid in the dissolution of the material in the solvent. As stated above, such co-solvents are selected from the same group of liquids above, as long as the co-solvent is different from the solvent in question in the particular embodiment in question and miscible with the primary solvent so as to effect dissolution of the material. Such co-solvents should be used as minimally as possible so as to avoid unnecessarily complicating the solid product (potentially mixed solvate crystal forms or mixed solvent amorphous associations, etc.), but there is no other reason to avoid them and their use is within the scope of the present invention. Where a co-solvent is utilized, it must also be one that is volatile or sublimates under the primary drying step conditions.

If desired, the solution pH may be adjusted within a range either to facilitate the solubility of the compound or to provide a particular pH environment for optimum stability that is compatible with the end use of the lyophilizate. Thus, for product that will be reconstituted with water for injection, with or without tonicity modifiers therein, the pH should be such that on reconstitution, a physiologically tolerated compatible pH is achieved. This is less of concern with materials that will be incorporated into more complex formulations or that will be used as reagents for further reactions. In these latter situations, the pH of the lyophilizate does not necessarily correlate with its end pH so that a larger latitude of pH values in the lyophilizate are acceptable.

In one embodiment of the invention, once the solution is obtained (and any desired pH adjustment and any desired filtration pre-material precipitation has taken place), the solution can be added to an anti-solvent for the material or can have such anti-solvent added to it. The purpose of this step is to force the material out of solution in a manner which will permit recovery of the desired form of the material. The anti-solvent is a substance which is not a solvent for the material, but is miscible with the solvent and, if present, any co-solvent, used. The anti-solvent must also be a substance that can be removed in the context of the freeze-drying itself. Thus, it is a substance which is volatile or sublimes at the temperature and pressure used in the primary drying step of the freeze-drying process. As stated above, the anti-solvent is selected from the same group of liquids set forth above, except that for use as an anti-solvent, the liquid must adhere to the constraints of this paragraph with respect to the particular material/solvent/optional co-solvent system in question.

In another embodiment of the invention, in which the material is hydrophobic or lipophilic, the solvent is selected from, 5-7 membered heteroring systems (the heteroring systems having 1-3 heteroatoms, where the heteroatoms are oxygen or sulfur, the sulfur atoms being unsubstituted or further carrying one or two oxygen substituents, except that two oxygen atoms cannot be in adjacent ring positions, for example tetra hydrofuran (THF), tetrahydropyran, dioxane, trioxane and other cyclic mono-, di- and tri-ethers). The use of these liquids as solvents in the lyophilization process is new to the lyophilization art. In addition, in the lyophilization of hydrophobic or lipophilic materials according to the invention, lower alkanols (methanol, ethanol, propanol, isopropanol, n-butanol, sec-butanol, or t-butanol), liquid ketones, liquid (oxygen or sulfur) ethers, liquid (oxygen or sulfur) ketones, liquid (oxygen or sulfur) esters or thioesters may also be used as the liquid solvent. In these embodiments, in addition to utilizing the anti-solvent as indicated above, the system can omit the anti-solvent and directly lyophilize the solution of the material in these liquids, in a manner completely analogously to completely aqueous lyophilization techniques. When omitting the anti-solvent, the preferred solvents are the heteroring solvents discussed above. The lyophilizate here as with the resultant lyophilizate of hydrophobic and lipophilic embodiments when using the anti-solvent process above do, however, require different reconstitution techniques than those for the hydrophilic materials.

Again, it should be noted that for any given material, not all of the liquids listed above will be solvents for the specific material, however, a mere solubility test will determine if the particular solvent is suitable for a particular material. If the material is soluble in the particular liquid, then the liquid is suitable as a solvent and/or co-solvent. If the material is not soluble in the liquid, then that is a potential anti-solvent for that system if and only if it is also miscible with the solvent or solvent/co-solvent system being used. Suppose a material has a solubility in a liquid A of 1000 mg/ml, in liquid B of 100 mg/ml, in liquid C of 10 mg/ml, and in liquid D of 0.01 mg/ml. Further, suppose that the material has a unit adult dose of 300 mg, a unit pediatric dose of 60 mg, and an infant unit dose of 12 mg. To prepare a suitable adult dose of the invention, one would use liquid A (and possibly liquid B) as the solvent. Liquid D is an clearly suitable as an anti-solvent, but liquid C might also be suitable as the anti-solvent. To prepare a suitable pediatric unit dose of the invention, one might use liquid A, but liquid B might be a better choice depending upon available equipment precision. Liquid C, while it can be used as the anti-solvent, since it can still dissolve an appreciable amount of the unit dose amount, it is preferably not so used, and the better choice as the anti-solvent is liquid D. In preparing a suitable infant unit dosage of the invention, liquid C is not only not suitable as the anti-solvent (since it is capable of dissolving virtually the entire unit dosage amount, but precisely because of this, it might actually be suitable for use as the solvent while liquid D would be the anti-solvent. Thus, given the particulars of the individual situation of the various solubilities in the various liquids as potential solvent and anti-solvents, and the specifics of the unit dosage amounts needed to be in the lyophilized product, a single liquid may be a solvent in some cases and yet an anti-solvent in others even for the same material intending to be lyophilized. Thus, while some testing is necessary to determine the specifics of the systems within the invention, such is well within the abilities of one of ordinary skill in the art. Generally, liquids that are suitable as solvent or co-solvents for hydrophilic materials are likely to be anti-solvents for hydrophobic or lipophilic materials, while anti-solvents for hydrophilic materials are likely to be solvents and co-solvents for hydrophobic and/or lipophilic materials. Similarly, liquids that are solvents and/or co-solvents for hydrophobic and/or lipophilic materials are likely to be anti-solvents for hydrophilic materials, while carriers that are anti-solvents for hydrophobic and/or lipophilic materials are likely to solvents or co-solvents for hydrophilic materials.

The material/solvent/co-solvent (if present)/anti-solvent (if present) system is then frozen and the frozen product is subjected to vacuum to sublimate or volatilize the solvent, so-solvent/anti-solvent components.

In general, in the embodiments in which anti-solvent is utilized, once the solution of the material is formed in the solvent or solvent/co-solvent mixture, the solution is mixed with anti-solvent in a proportion in the range of about 5:1 to about 1:5, preferably about 4:1 to about 1:4, more preferably about 3:1 to about 1:3; even more preferably about 2:1 to about 1:2, still more preferably about 1.5:1 to about 1:1.5, still even more preferably about 1:1 on a volume/volume basis of (solvent and/or-solvent):(anti-solvent).

The addition of the anti-solvent causes the material to come out of solution. This precipitation can be allowed to continue for as long as desired before the freezing step takes place, but the slower the precipitation, the greater the likelihood that the precipitated material will adopt a crystalline conformation. The speed of precipitation and thus the degree of crystallinity or amorphous character can be controlled by the ratio of anti-solvent to solvent/co-solvent utilized as well as the speed of the addition when adding anti-solvent to the solvent/co-solvent/material solution as well as freezing conditions. The reverse addition of solvent/co-solvent/material to anti-solvent results in a very rapid precipitation since the ratio of anti-solvent to solvent/co-solvent is always very high during the addition.

Once the precipitation is effected (or once the dissolution is effected in the embodiments that omit the anti-solvent), the mixture is frozen in a cooling step that is typically over a period of about 30 min to 10 hours, preferably about 1 our to about 8 hours, more preferably about 2 hours to about 7 hours, typically about 4 to about 6 hours to result in a frozen mass. A quick freezing generally favors amorphous product, while a slow cooling generally favors a more crystalline product; however, this is only a general guideline, and particular results can vary depending on a number of conditions. If desired, prior to freezing, the mixture can be filtered so that the bulk of the solvent/co-solvent/anti-solvent is removed/recovered leaving behind a precipitate wet with some of the solvent/co-solvent/anti-solvent mixture, which is then subjected to the freezing step. (This procedure applies especially when preparing sterile bulk, not unit dose vials for parenteral administration).

Once frozen, the mass is subjected to a vacuum pressure whereby a substantial portion, if not all of the remaining solvent/co-solvent/anti-solvent is volatilized off during primary drying. Remaining residual amounts of one or more of solvent and/or co-solvent and/or anti-solvent are removed in a secondary drying step. Generally, during the primary drying the product temperature is maintained below 0° C while in the secondary drying the product temperature will be maintained at about 25 to 40° C., although other primary and secondary drying temperatures may be suitably found in the ordinary course by those of ordinary skill in the art.

The lyophilizates prepared according to the invention can be prepared in situ in the container that will be used for reconstitution; in molds (or blister packs) for preparing rapidly dissolving tablets; or can be prepared in bulk for use in any other processes or reactions as desired. Thus, bulk chemicals can be prepared and packaged for blending with other components at a user's convenience or need. Similarly small portions of lyophilizates of the invention may be prepared in unit of use containers and packed with dissolution media in suitable kits for ease of preparing single units of use.

In one particularly preferred embodiment, amifostine (a highly water soluble material) is the hydrophilic material, water is selected as the solvent, and tetrahydrofuran is selected as the anti-solvent. Also, tetrahydropyran, dioxane, trioxane and the other liquid heteroring compounds mentioned in paragraphs 0034-0036 can be used as anti-solvents for amifostine when water is the solvent. Of the aforementioned solvents, dioxane offers special advantages over other organic solvents. Dioxane freezes below 15° C and sublimates rapidly under vacuum. Use of dioxane as an anti-solvent does not require any solvent trap and can be lyophilized similar to completely aqueous lyophilization. Similarly trioxane also has a low meting point and can be easily removed during the lyophilization. Optionally, the pH can be adjusted to into the range of about 7 to about 8 prior to adding the anti-solvent.

In another preferred embodiment, a slurry is made using ceftazadime and water. The pH is adjusted to about 5 to about 7 using NaOH to facilitate the dissolution of ceftazidime. Once solution is effected, an anti-solvent, such as THF, dioxane or one of the other liquid heteroring compounds is added to precipitate the ceftazadime, which is then frozen and dried.

In this embodiment, lower alkanols, such as ethanol, n- or iso-propanol, or n-, sec-, or t-butanol may also be used as the anti-solvent. The same procedure is generally applicable to other cephalosporins, especially to ceftrioxone and cephradine.

In another embodiment, a slurry of cefapime is made in water. The pH is adjusted to about 1 to about 3 with HCl (or other suitable inorganic acid) to facilitate dissolution. Once dissolved, anti-solvent (liquid herteroring compounds) is added to precipitate the cefapime, and the result is freeze dried.

In a further embodiment, cyclophosphamide (sparingly soluble in water but highly soluble in ethanol) is dissolved in one or more of the liquid hetero-ring compounds and/or lower alkanols to form a concentrated solution. Water is then added as an anti-solvent to precipitate the crystalline cyclophosphamide monohydrate or anhydrate. The result is then freeze-dried.

In another particularly preferred embodiment, itraconazole is the hydrophobic/lipophilic material and a non-aqueous liquid is selected as a solvent to dissolve it. An anti-solvent is not needed to lyophilize the hydrophobic/lipophilic molecule. The non-aqueous solvents to dissolve lipophilic molecules are listed in paragraph 0034-0036. In addition ethanol and PEG 600-6000 and tocopherol succinate and acetate can also be used as solvents to solubilize lipophilic materials. Once the material is dissolved in the non-aqueous solvent, it is filtered aseptically to remove any undesired components and microorganisms and filled into vials and lyophilized either using the conventional lyophilization procedures or special procedures depending on the nature and amount of non-aqueous solvents used to dissolve the material. The lyophilizate can be reconstituted with minimum volume of pharmaceutically acceptable solvent (typically polyethylene glycol or liquid PEGs) to prepare a liquid concentrate. The liquid concentrate is further diluted to a desirable concentration in a special diluent or commercially available Intralipid fat emulsions, or plasma or serum or in whole blood prior to administering to patients. One aspect of the novelty of this embodiment of the invention is that patient's blood can be used to dilute the liquid concentrate and administer back into the patients blood stream. Since these molecules are lipophilic, they will partition into the lipid layer of the fat emulsion or blood.

In a still further embodiment, itraconazole is dissolved in non-aqueous liquid such as THF at a very high concentration. Itraconazole is generally considered soluble in methylene chloride only. We surprisingly found that high concentrations of itraconazole can be dissolved in the non-aqueous solvents listed in the paragraph 0034-0036 in the presence of small quantities of HCl. The itraconazole thus dissolved in the non aqueous solvent is lyophilized. The lyophilizate is reconstituted to 100 mg/ml solution using pharmaceutically acceptable solvent, typically propylene glycol. The liquid concentrate is further diluted with 25 ml or more of 10% Intralipid fat emulsion. The aqueous and oil phase of the emulsion is separated by using an ultracentrifuge and it is observed that all the itraconazole is partitioned into the fat layer of the emulsion.

While some embodiments seek to eliminate auxiliary components in the lyophilization process, not all auxiliaries need be eliminated. Thus, as desired, the solution prepared prior to any precipitation of the material and prior to any freezing step can have suitable auxiliary materials such as building agents, buffers, and anti-oxidizing agents. Each of the auxiliary agents must be compatible with the end use or be capable of being removed prior to use (as when the lyophilizate is being used in further reactions or where the subsequently purified product will have the non-acceptable material removed prior to that product being used). Bulking agents that are generally suitable are those which raise the glass transition temperature of the material being lyophilized. For pharmaceuticals these generally include, but are not limited to, saccharides (such as fructose, sucrose, lactose, trehalose, and others), polyvinylpyrrolidone, and cyclodextrins, the saccharides being preferred, and trehalose being a particularly suitable material. Complexing/solubilizing agents include niacinamide and other cyclic amide, gentisic acid, cyclodextrins and surfactants with HLB values ranging from 1 to 16. Nonetheless, in most instances, the invention permits the omission of the bulking agent, and the absence of bulking agent is a preferred embodiment. For pharmaceutical purposes, buffers can be, but are not limited to, amino acids, inorganic buffers, mono- and di-carboxylic acid buffers, hydroxyl-mono- and di-carboxylic acid buffers, amines, and sulfonamides. The antioxidants include, but are not limited to, different class of bisulfites, ascorbic acid, disodium- and tetrasodium EDTA, citrates as metal ion chelators, BHA, BHT, sulfoxylates, propyl gallate, amino acids containing thio group such as methionine, and thiols as well as other antioxidants listed in the FDA website for inactive ingredients used in pharmaceutical dosage forms.

Lyophilizates of the present invention have significantly improved stability over materials prepared without lyophilization or prepared via current lyophilization techniques other than those of the invention. For example, a completely water lyophilization of amifostine results in a material that degrades to 80% of its initial amifostine amount in 30 days, when stored at 40° C. Amorphous amifostine lyophilizate of the invention using water as the solvent and tetrahydrofuran as the anti-solvent, stored under the same conditions, results in degrading to only 98% of its initial amount in 30 days and to 90% of its initial amount in 90 days.

The lyophilizates of the present invention (when limited to pharmaceutical and veterinary active agents, as previously discussed, can be utilized in the preparation of injectable final products as well as in rapidly dissolving oral dosage forms. In addition, they can be utilized in the preparation of other oral dosage forms (tablets, capsules, powders, etc) for ingestion as is or for rapid dissolution in liquids for ingestion. Still further, the lyophilizates can be applied topically as is to wet or "weeping/oozing" surfaces for administration. These include, without limitation topical application to open or oozing wounds, as well as to mucous membranes. Inhalation of lyophilizate powder for application to the nose and bronchial tree, as well as instillation of the powder to the eye, oral mucosa, rectum, vaginal, uterine, urethral, and urinary bladder tissues are contemplated by the present invention. In addition, the lyophilzates can be rapidly dissolved in appropriate liquid media for administration to these tissues as well.

EXAMPLES

Example 1

A sufficient amount of amifostine is dissolved in water to result in a concentration in the range of 100 to 500 mg/ml. The solution is asceptically filtered through a 0.2 micron filter (Pall filter membrane Nylon 66 or any compatible filter). Separately, tetrahydrofuran is asceptically filtered using a Pall filter membrane Nylon 66. 2 ml of the filtered amifostine solution is placed in a 5 ml USP type 1 pre-sterilized and depyrogenated flint vial and 1 ml of the filtered THF is added thereto. The vial contents become cloudy. The vials having the amifostine, water, and THF are placed onto a lyophilization tray, which is then introduced into a lyophilization chamber. The chamber temperature is set to −30° C. When the product temperature reaches −25° C., the condenser is turned on at a setting of −50° C. or below. When the condenser temperature reaches −40° C., the vacuum pump is turned on and the vacuum monitor gauge is adjusted to 200 microns. When the vacuum reaches 200 microns, the shelf temperature is set to −5° C. and the product is dried for 12 hours. At the conclusion of the 12 hours, the shelf temperature is reset to 30° C. and the product is dried for an additional 15 hours. The equipment is bleeded with nitrogen to bring the pressure back to atmospheric pressure, the vials are stoppered, and sealed with aluminum caps.

Example 2

Example 1 is repeated with the following variations as set forth in Table I

TABLE I

| SAMPLE | AMIFOSTINE AMOUNT | THF AMOUNT | FREEZE TEMP | PRIMARY DRY TIME | SECONDARY DRY TIME |
| --- | --- | --- | --- | --- | --- |
| A | 100 mg | 0.1 ml | −40° | 12 HOURS | 12 HOURS |
| B | 200 mg | 0.1 ml | −40° | 20 HOURS | 20 HOURS |
| C | 300 mg | 0.1 ml | −40° | 12 HOURS | 12 HOURS |
| D | 400 mg | 0.1 ml | −40° | 12 HOURS | 12 HOURS |
| E | 500 mg | 0.1 ml | −40° | 12 HOURS | 12 HOURS |
| F | 100 mg | 0.25 ml | −30° | 15 HOURS | 15 HOURS |
| G | 200 mg | 0.25 ml | −30° | 15 HOURS | 15 HOURS |
| H | 300 mg | 0.25 ml | −20° | 18 HOURS | 15 HOURS |
| I | 400 mg | 0.25 ml | −20° | 18 HOURS | 15 HOURS |
| J | 500 mg | 0.25 ml | −40° | 20 HOURS | 15 HOURS |
| K | 100 mg | 0.5 ml | −35° | 20 HOURS | 15 HOURS |
| L | 200 mg | 0.5 ml | −350° | 14 HOURS | 18 HOURS |
| M | 300 mg | 0.5 ml | −20° | 14 HOURS | 18 HOURS |
| N | 400 mg | 0.5 ml | −25° | 13 HOURS | 18 HOURS |
| O | 500 mg | 0.5 ml | −25° | 13 HOURS | 18 HOURS |
| P | 100 mg | 1 ml | −20° | 12 HOURS | 18 HOURS |
| Q | 200 mg | 1 ml | −30° | 15 HOURS | 15 HOURS |
| R | 300 mg | 1 ml | −30° | 15 HOURS | 15 HOURS |
| S | 400 mg | 1 ml | −20° | 18 HOURS | 15 HOURS |
| T | 500 mg | 1 ml | −20° | 18 HOURS | 15 HOURS |
| U | 100 mg | 2 ml | −40° | 20 HOURS | 15 HOURS |
| V | 200 mg | 2 ml | −35° | 20 HOURS | 15 HOURS |
| W | 300 mg | 2 ml | −350° | 14 HOURS | 18 HOURS |
| X | 400 mg | 2 ml | −20° | 14 HOURS | 18 HOURS |
| Y | 500 mg | 2 ml | −25° | 13 HOURS | 18 HOURS | whereby suitable lyophilizates can be obtained.

Example 3

Example 2 is repeated using dioxane as the anti-solvent, whereby suitable lyophilizates can be obtained.

Examples 4-7

Examples 2-3 are repeated except that amifostine is replaced (a) with ceftazadine with the water having a pH of 5-7 (Examples 4-5) or (b) with cefapine with the water having a pH of 1-3, whereby suitable lyophilizates can be obtained.

Example 8

A sufficient amount of itraconazole is dissolved in acidified tetrahydrofuran to result in a concentration in the range of 100 to 500 mg/ml. The solution is asceptically filtered through a 0.2 micron filter (Pall filter membrane Nylon 66 or any compatible filter). Separately, water is asceptically filtered using a Pall filter membrane Nylon 66 (or any compatible filter). 2 ml of the filtered itraconazole solution is placed in a 5 ml USP type 1 pre-sterilized and depyrogenated flint vial and 1 ml of the filtered water is added thereto. The vial contents become cloudy. The vials having the itraconazole, water, and THF are placed onto a lyophilization tray, which is then introduced into a lyophilization chamber. The chamber temperature is set to −30° C. When the product temperature reaches −25° C., the condenser is turned on at a setting of −50° C. or below. When the condenser temperature reaches −40° C., the vacuum pump is turned on and the vacuum monitor gauge is adjusted to 200 microns. When the vacuum reaches 200 microns, the shelf temperature is set to −5° C. and the product is dried for 12 hours. At the conclusion of the 12 hours, the shelf temperature is reset to 30° C. and the product is dried for an additional 15 hours. The equipment is bleeded with nitrogen to bring the pressure back to atmospheric pressure, the vials are stoppered, and sealed with aluminum caps.

Example 9

Example 8 is repeated with the following variations as set forth in Table II

TABLE II

| SAMPLE | INTRACONAZOLE AMOUNT | THF AMOUNT | FREEZE TEMP | PRIMARY DRY TIME | SECONDARY DRY TIME |
| --- | --- | --- | --- | --- | --- |
| A | 100 mg | 1 ml | −40° | 12 HOURS | 12 HOURS |
| B | 200 mg | 2 ml | −40° | 20 HOURS | 20 HOURS |
| C | 300 mg | 3 ml | −40° | 12 HOURS | 12 HOURS |

TABLE II-continued

| SAMPLE | INTRACONAZOLE AMOUNT | THF AMOUNT | FREEZE TEMP | PRIMARY DRY TIME | SECONDARY DRY TIME |
|---|---|---|---|---|---|
| D | 400 mg | 4 ml | −40° | 12 HOURS | 12 HOURS |
| E | 500 mg | 5 ml | −40° | 12 HOURS | 12 HOURS |
| F | 100 mg | 1 ml | −30° | 15 HOURS | 15 HOURS |
| G | 200 mg | 2 ml | −30° | 15 HOURS | 15 HOURS |
| H | 300 mg | 3 ml | −20° | 18 HOURS | 15 HOURS |
| I | 400 mg | 4 ml | −20° | 18 HOURS | 15 HOURS |
| J | 500 mg | 5 ml | −40° | 20 HOURS | 15 HOURS |
| K | 100 mg | 1 ml | −35° | 20 HOURS | 15 HOURS |
| L | 200 mg | 2 ml | −350° | 14 HOURS | 18 HOURS |
| M | 300 mg | 3 ml | −20° | 14 HOURS | 18 HOURS |
| N | 400 mg | 4 ml | −25° | 13 HOURS | 18 HOURS |
| O | 500 mg | 5 ml | −25° | 13 HOURS | 18 HOURS |
| P | 100 mg | 1 ml | −20° | 12 HOURS | 18 HOURS |
| Q | 200 mg | 2 ml | −30° | 15 HOURS | 15 HOURS |
| R | 300 mg | 3 ml | −30° | 15 HOURS | 15 HOURS |
| S | 400 mg | 4 ml | −20° | 18 HOURS | 15 HOURS |
| T | 500 mg | 5 ml | −20° | 18 HOURS | 15 HOURS |
| U | 100 mg | 1 ml | −40° | 20 HOURS | 15 HOURS |
| V | 200 mg | 2 ml | −35° | 20 HOURS | 15 HOURS |
| W | 300 mg | 3 ml | −350° | 14 HOURS | 18 HOURS |
| X | 400 mg | 4 ml | −20° | 14 HOURS | 18 HOURS |
| Y | 500 mg | 5 ml | −25° | 13 HOURS | 18 HOURS | whereby suitable lyophilizates can be obtained.

Example 10

Example 9 is repeated using dioxane as the solvent w whereby suitable lyophilizates can be obtained.

Examples 11-12

Examples 9-10 are repeated except that the water antisolvent is omitted, whereby suitable lyophilizates can be obtained.

Example 13-17

Example 9 is repeated using ethanol (Example 13), tetrahydropyrane (Example 14), isopropanol (Example 15), tocopherol acetate (Example 16), or tocopherol succinate (Example 17) as the solvent whereby suitable lyophilizates can be obtained.

I claim:

1. A method of lyophilizing a hydrophilic pharmaceutical compound comprising:
   (a) dissolving the hydrophilic pharmaceutical compound in one or more hydrophilic solvents to form a solution, wherein the one or more hydrophilic solvents is a liquid in which the hydrophilic pharmaceutical compound dissolves;
   (b) adding one or more lipophilic non-solvents for the hydrophilic pharmaceutical compound to the solution, wherein:
      (i) the one or more lipophilic non-solvents is a liquid in which the hydrophilic pharmaceutical compound is essentially insoluble,
      (ii) the one or more lipophilic non-solvents is miscible with the one or more hydrophilic solvents,
      (iii) the one or more lipophilic non-solvents is volatilizable under freeze-drying conditions, and
      (iv) the hydrophilic pharmaceutical compound at least partially precipitates;
   (c) freezing the hydrophilic pharmaceutical compound, the one or more hydrophilic solvents and the one or more lipophilic non-solvents of step (b) to yield a frozen result, the frozen result comprising a frozen portion; and
   (d) vacuum drying the frozen result of step (c) to yield a lyophilizate.

2. The method of claim 1 wherein the hydrophilic pharmaceutical compound is crystalline.

3. The method of claim 1 wherein the hydrophilic pharmaceutical compound is amorphous.

4. The method of claim 1 wherein the lyophilizate is crystalline.

5. The method of claim 1 wherein the lyophilizate is amorphous.

6. The method of claim 1, further comprising at least one of (i) aseptically filtering the solution of step (a) prior to the addition of the lipophilic non-solvent thereto; and (ii) aseptically filtering the lipophilic non-solvent prior to the addition of the lipophilic non-solvent to the solution of step (a).

7. The method of claim 1 wherein the hydrophilic solvent is water.

8. The method of claim 1 wherein the hydrophilic solvent is a lower alkanol.

9. The method of claim 8 wherein the lower alkanol is ethanol, propanol, isopropanol, sec-butanol, t-butyl alcohol, or n-butyl alcohol.

10. The method of claim 1 wherein the lipophilic non-solvent is a cyclic mono-, di-, or tri-ether.

11. The method of claim 10 wherein the cyclic mono-, di-, or tri-ether is tetrahydrofuran, tetrahydropyran, dioxane, or trioxane.

12. The method of claim 1, further comprising adding a co-solvent to the hydrophilic solvent.

13. The method of claim 12 wherein the co-solvent is selected from the group consisting of polyethylene glycol 600-6000.

14. The method of claim 1, further comprising adding a bulking agent.

15. The method of claim 14 wherein the bulking agent is selected from the group consisting of a saccharide, polyvinylpyrrolidone, a cyclodextrin, and trehalose.

16. The method of claim 1, further comprising adding a solubilizer, a surfactant or a combination thereof.

17. The method of claim 16 wherein the solubilizer is selected from the group consisting of a cyclic amide, gentisic acid, and a cyclodextrin.

18. The method of claim 16, wherein the surfactant comprises a hydrophilic-lipophilic balance (HLB) value ranging from 1 to 16.

19. The method of claim 1, further comprising adding a buffer.

20. The method of claim 19, wherein the buffer is selected from the group consisting of an amino acid, an inorganic buffer, a mono- or di-carboxylic acid buffer, a hydroxyl-mono- or di-carboxylic acid buffer, an amine, and a sulfonamide.

21. The method of claim 1, further comprising adding an antioxidant.

22. The method of claim 21 wherein the antioxidant is selected from the group consisting of a bisulfite, ascorbic acid, disodium- or tetrasodium ethylenediaminetetraacetic acid, a citrate as metal ion chelator, butylated hydroxyanisole, butylated hydroxytoluene, a sulfoxylate, propyl gallate, an amino acid containing a thio group, and a thiol.

23. The method of claim 1 wherein the frozen result further comprises an unfrozen portion.

24. A method of lyophilizing a lipophilic pharmaceutical compound comprising:
  (a) dissolving the lipophilic pharmaceutical compound in one or more lipophilic solvents to form a solution, wherein the one or more lipophilic solvents is a liquid in which the lipophilic pharmaceutical compound dissolves;
  (b) adding one or more hydrophilic non-solvents for the lipophilic pharmaceutical compound to the solution, wherein:
    (i) the one or more hydrophilic non-solvents is a liquid in which the lipophilic pharmaceutical compound is essentially insoluble,
    (ii) the one or more hydrophilic non-solvents is miscible with the one or more lipophilic solvents,
    (iii) the one or more hydrophilic non-solvents is volatilizable under freeze-drying conditions, and
    (iv) the lipophilic pharmaceutical compound at least partially precipitates;
  (c) freezing the lipophilic pharmaceutical compound, the one or more lipophilic solvents and the one or more hydrophilic non-solvents of step (b) to yield a frozen result, the frozen result comprising a frozen portion; and
  (d) vacuum drying the frozen result of step (c) to yield a lyophilizate.

25. The method of claim 24 wherein the lipophilic pharmaceutical compound is crystalline.

26. The method of claim 24 wherein the lipophilic pharmaceutical compound is amorphous.

27. The method of claim 24 wherein the lyophilizate is crystalline.

28. The method of claim 24 wherein the lyophilizate is amorphous.

29. The method of claim 24, further comprising at least one of (i) aseptically filtering the solution of step (a) prior to the addition of the hydrophilic non-solvent thereto; and (ii) aseptically filtering the hydrophilic non-solvent prior to the addition of the lipophilic non-solvent to the solution of step (a).

30. The method of claim 24 wherein the hydrophilic non-solvent is water.

31. The method of claim 24 wherein the hydrophilic non-solvent is a lower alkanol.

32. The method of claim 31 wherein the lower alkanol is ethanol, propanol, isopropanol, sec-butanol, t-butyl alcohol, or n-butyl alcohol.

33. The method of claim 24 wherein the lipophilic solvent is a cyclic mono-, di-, or tri-ether.

34. The method of claim 33 wherein the cyclic mono-, di-, or tri-ether is tetrahydrofuran, tetrahydropyran, dioxane, or trioxane.

35. The method of claim 24, further comprising adding a co-solvent to the lipophilic solvent.

36. The method of claim 35 wherein the co-solvent is selected from the group consisting of polyethylene glycol 600-6000.

37. The method of claim 24, further comprising adding a bulking agent.

38. The method of claim 37 wherein the bulking agent is selected from the group consisting of a saccharide, polyvinylpyrrolidone, a cyclodextrin, and trehalose.

39. The method of claim 24, further comprising adding a solubilizer, a surfactant or a combination thereof.

40. The method of claim 39 wherein the solubilizer is selected from the group consisting of a cyclic amide, gentisic acid, and a cyclodextrin.

41. The method of claim 39, wherein the surfactant comprises a hydrophilic-lipophilic balance (HLB) value ranging from 1 to 16.

42. The method of claim 24, further comprising adding a buffer.

43. The method of claim 42, wherein the buffer is selected from the group consisting of an amino acid, an inorganic buffer, a mono- or di-carboxylic acid buffer, a hydroxyl-mono- or di-carboxylic acid buffer, an amine, and a sulfonamide.

44. The method of claim 24, further comprising adding an antioxidant.

45. The method of claim 44 wherein the antioxidant is selected from the group consisting of a bisulfite, ascorbic acid, disodium- or tetrasodium ethylenediaminetetraacetic acid, a citrate as metal ion chelator, butylated hydroxyanisole, butylated hydroxytoluene, a sulfoxylate, propyl gallate, an amino acid containing a thio group, and a thiol.

46. The method of claim 24 wherein the frozen result further comprises an unfrozen portion.

\* \* \* \* \*